US011136351B2

(12) United States Patent
Clark et al.

(10) Patent No.: US 11,136,351 B2

(45) Date of Patent: Oct. 5, 2021

(54) ALPHA CONOTOXIN PEPTIDES

(71) Applicant: THE UNIVERSITY OF QUEENSLAND, St Lucia (AU)

(72) Inventors: Richard James Clark, Chapel Hill (AU); James Travis Daniel, Upper Mount Gravatt (AU)

(73) Assignee: The University of Queensland, Queensland (AU)

(*) Notice: Subject to any disclaimer, the term of this patent is extended or adjusted under 35 U.S.C. 154(b) by 0 days.

(21) Appl. No.: 15/998,725

(22) PCT Filed: Feb. 16, 2017

(86) PCT No.: PCT/AU2017/050135

§ 371 (c)(1),
(2) Date: Aug. 16, 2018

(87) PCT Pub. No.: WO2017/139845

PCT Pub. Date: Aug. 24, 2017

(65) Prior Publication Data

US 2020/0247848 A1 Aug. 6, 2020

(30) Foreign Application Priority Data

Feb. 16, 2016 (AU) ................................ 2016900528

(51) Int. Cl.

| | |
|---|---|
| ***C07K 7/06*** | (2006.01) |
| ***A61P 25/00*** | (2006.01) |
| ***C07K 7/08*** | (2006.01) |
| *A61K 38/00* | (2006.01) |

(52) U.S. Cl.

CPC ................ *C07K 7/06* (2013.01); *A61P 25/00* (2018.01); *C07K 7/08* (2013.01); *A61K 38/00* (2013.01)

(58) Field of Classification Search

CPC ...... C07K 7/06; C07K 7/08; C07K 14/43504; A61P 25/00; A61P 9/12; A61P 9/10; A61P 29/00; A61P 25/32; A61P 25/30; A61P 25/28; A61P 25/24; A61P 25/18; A61P 25/16; A61P 25/08; A61P 25/04; A61P 11/08; A61K 38/00

See application file for complete search history.

(56) References Cited

U.S. PATENT DOCUMENTS

| | | | |
|---|---|---|---|
| 6,113,911 | A | 9/2000 | Binz et al. |
| 6,797,808 | B1 | 9/2004 | Watkins et al. |
| 2005/0203025 | A1 | 9/2005 | Blaschuk et al. |

FOREIGN PATENT DOCUMENTS

| | | |
|---|---|---|
| AU | 2006236006 | 11/2007 |
| WO | 03/010317 | 2/2003 |
| WO | 2015/013169 | 1/2015 |

OTHER PUBLICATIONS

Bowie et al (Science, 1990, 247:1306-1310) (Year: 1990).*

Burgess et al (J. Cell Biol. 111:2129-2138, 1990) (Year: 1990).*

Lazar et al (Mol. Cell. Biol., 8:1247-1252, 1988) (Year: 1988).*

International Search Report for PCT/AU2017/050135, dated Apr. 10, 2017, 6 pages.

Written Opinion of the ISA for PCT/AU2017/050135, dated Apr. 10, 2017, 5 pages.

Satkunanathan, N., et al., "Alpha-conotoxin Vc1.1 Alleviates Neuropathic Pain and Accelerates Functional Recovery of Injured Neurons", Brain Research, 2005, vol. 1059, pp. 149-158.

Lou, S., et al., "Characterization of a Novel alpha-Conotoxin TxID from Conus textile That Potently Blocks Rat alpha3beta4 Nicotinic Acetylcholine Receptors", Journal of Medicinal Chemistry, 2013, vol. 56, pp. 9655-9663.

Macraild, C., et al., "Structure and Activity of (2,8)-Dicarba-(3,12)-cystino alpha-ImI, an alpha-Conotoxin Containing a Nonreducible Cystine Analogue", 2009, vol. 52, pp. 755-762.

Chun, J., et al., "Cone Snail Milked Venom Dynamics—A quantitative study of Conus purpurascens", Toxicon, 2012, vol. 60, pp. 83-94.

Hansson, K., "The First gamma-Carboxyglutamic Acid-containing Contryphan", Journal of Biological Chemistry, 2004, vol. 279, No. 31, pp. 32453-32463.

Carstens, B., et al., "Structure-Activity Studies of Cysteine-Rich alpha-Conotoxins that Inhibit High-Voltage-Activated Calcium Channels via GABA B Receptor Activation Reveal a Minimal Functional Motif", Angewandte Chemie International, 2016, vol. 55, pp. 4692-4696.

Yu, R., et al., "Less is More: Design of a Highly Stable Disulfide-Deleted Mutant of analgesic Cyclic α-Conotoxin VC1.1," Scientific Reports, (2015)5:13264, pp. 1-11.

Lamthanh, H., et al., "Minimal conformation of the α-conotoxin ImI for the α7 neuronal nicotinic acetylcholine receptor recognition correlated CD, NMR, and binding studies," FEBS Letters 454 (1999), pp. 296-298.

* cited by examiner

*Primary Examiner* — Sudhakar Katakam

(74) *Attorney, Agent, or Firm* — Nixon & Vanderhye, PC

(57) ABSTRACT

The invention relates to alpha conotoxin (α-conotoxin) peptides and methods for their preparation. Also described are pharmaceutical compositions comprising alpha conotoxin (α-conotoxin) peptides and their use in the treatment or prevention of indications 5 associated with nicotinic acetylcholine receptors and/or voltage gated calcium channels.

16 Claims, 9 Drawing Sheets

Specification includes a Sequence Listing.

| Name/ Prefix | Sequence/ Structure[a] | Mass (Da)[b] | Observed Mass | Folding Protocol | Sequence/ Structure | Observed Mass[c] | Δ Mass (Da) | HPLC[d] |
|---|---|---|---|---|---|---|---|---|
| [R7A] Vc1.1 (1-8) | GCSSDPAC* SEQ ID NO: 12 | 737.8 |   | 0.1 M $NH_4HCO_3$; 2 mM DPDS in $CH_3OH$; 2 hr @ RT |  GCSSDPAC* SEQ ID NO: 12 |   | -2 |  |
| [R7A] Vc1.1 (2-8) | CSSDPAC* SEQ ID NO: 48 | 765.8 |   | 0.1 M $NH_4HCO_3$; 2 mM DPDS in $CH_3OH$; 2 hr @ RT |  CSSDPAC* SEQ ID NO: 48 |   | -2 |  |
| Retro-inverso Vc1.1 (1-8) | crpdsscg* SEQ ID NO: 47 | 822.9 |   | 0.1 M $NH_4HCO_3$; 2 mM DPDS in $CH_3OH$; 2 hr @RT |  crpdsscg* SEQ ID NO: 47 |   | -2 |  |

SEQUENCE LISTING

<160> NUMBER OF SEQ ID NOS: 47

<210> SEQ ID NO 1
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: Xaa1
<222> LOCATION: (1)..(1)
<223> OTHER INFORMATION: Xaa1 is selected from any amino acid or is absent
<220> FEATURE:
<221> NAME/KEY: Xaa2
<222> LOCATION: (2)..(2)
<223> OTHER INFORMATION: Xaa2 is selected from any amino acid residue wherein the side chains of the amino acids form a linker when Xaa2 and Xaa7 are taken together
<220> FEATURE:
<221> NAME/KEY: Xaa3
<222> LOCATION: (3)..(3)
<223> OTHER INFORMATION: Xaa3 is selected from any amino acid
<220> FEATURE:
<221> NAME/KEY: Xaa4
<222> LOCATION: (4)..(4)
<223> OTHER INFORMATION: Xaa4  is selected from any amino acid
<220> FEATURE:
<221> NAME/KEY: Xaa5
<222> LOCATION: (5)..(5)
<223> OTHER INFORMATION: Xaa5  is selected from any amino acid
<220> FEATURE:
<221> NAME/KEY: Xaa6
<222> LOCATION: (7)..(7)
<223> OTHER INFORMATION: Xaa6  is selected from any amino acid
<220> FEATURE:
<221> NAME/KEY: Xaa7
<222> LOCATION: (8)..(8)
<223> OTHER INFORMATION: Xaa7 is selected from any amino acid residue wherein the side chains of the amino acids form a linker when Xaa2 and Xaa7 are taken together

<400> SEQUENCE: 1

```
Xaa Xaa Xaa Xaa Xaa Pro Xaa Xaa
1               5
```

<210> SEQ ID NO 2
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: Xaa1
<222> LOCATION: (1)..(1)
<223> OTHER INFORMATION: Xaa1 is selected from any amino acid or is absent
<220> FEATURE:
<221> NAME/KEY: Xaa4
<222> LOCATION: (4)..(4)
<223> OTHER INFORMATION: Xaa4 is selected from any amino acid
<220> FEATURE:
<221> NAME/KEY: Xaa5
<222> LOCATION: (5)..(5)
<223> OTHER INFORMATION: Xaa5 is selected from any amino acid
<220> FEATURE:
<221> NAME/KEY: Xaa6
<222> LOCATION: (7)..(7)
<223> OTHER INFORMATION: Xaa6 is selected from any amino acid

<400> SEQUENCE: 2

```
Xaa Cys Ser Xaa Xaa Pro Xaa Cys
1               5
```

<210> SEQ ID NO 3
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: Xaa4
<222> LOCATION: (4)..(4)
<223> OTHER INFORMATION: Xaa4 is selected from any amino acid
<220> FEATURE:
<221> NAME/KEY: Xaa5
<222> LOCATION: (5)..(5)
<223> OTHER INFORMATION: Xaa5 is selected from any amino acid
<220> FEATURE:
<221> NAME/KEY: Xaa6
<222> LOCATION: (7)..(7)
<223> OTHER INFORMATION: Xaa6 is selected from any amino acid

<400> SEQUENCE: 3

Gly Cys Ser Xaa Xaa Pro Xaa Cys
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Cys Ser Ser Asp Pro Arg Cys
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Gly Cys Ser Ala Asp Pro Arg Cys
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Gly Cys Ser Lys Asp Pro Arg Cys
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Gly Cys Ser Asn Asp Pro Arg Cys
1               5

<210> SEQ ID NO 8
<211> LENGTH: 8

<212> TYPE: PRT
<213> ORGANISM: Artificial Sequence
<220> FEATURE:
<223> OTHER INFORMATION: Synthetic

<400> SEQUENCE: 8

Gly Cys Ser Thr Asp Pro Arg Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Gly Cys Ser His Asp Pro Arg Cys
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Gly Cys Ser Arg Asp Pro Arg Cys
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Gly Cys Ser Ser Ala Pro Arg Cys
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Gly Cys Ser Ser Asp Pro Ala Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Gly Cys Ser Ser Asn Pro Ala Cys
1               5

<210> SEQ ID NO 14
<211> LENGTH: 8
<212> TYPE: PRT

<213> ORGANISM: Artificial Sequence
<220> FEATURE:
<223> OTHER INFORMATION: Synthetic

<400> SEQUENCE: 14

Gly Cys Ser Ser Asp Pro Arg Cys
1 5

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Gly Cys Ser Ser His Pro Ala Cys
1 5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Gly Cys Ser Ser Tyr Pro Pro Cys
1 5

<210> SEQ ID NO 17
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: Xaa1
<222> LOCATION: (1)..(1)
<223> OTHER INFORMATION: Xaa1 is selected from any amino acid or is absent
<220> FEATURE:
<221> NAME/KEY: Xaa5
<222> LOCATION: (5)..(5)
<223> OTHER INFORMATION: Xaa5 is selected from any amino acid
<220> FEATURE:
<221> NAME/KEY: Xaa6
<222> LOCATION: (7)..(7)
<223> OTHER INFORMATION: Xaa6 is selected from any amino acid

<400> SEQUENCE: 17

Xaa Cys Ser Ser Xaa Pro Xaa Cys
1 5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Ala Cys Ser Ser Asp Pro Arg Cys
1 5

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Cys Ser Ser Asp Pro Arg Cys
1 5

<210> SEQ ID NO 20
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: Xaa3
<222> LOCATION: (3)..(3)
<223> OTHER INFORMATION: Xaa3 is selected from any amino acid
<220> FEATURE:
<221> NAME/KEY: Xaa5
<222> LOCATION: (5)..(5)
<223> OTHER INFORMATION: Xaa5 is selected from any amino acid
<220> FEATURE:
<221> NAME/KEY: Xaa6
<222> LOCATION: (7)..(7)
<223> OTHER INFORMATION: Xaa6 is selected from any amino acid

<400> SEQUENCE: 20

Gly Cys Xaa Ser Xaa Pro Xaa Cys
1 5

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Gly Cys Asp Ser Asp Pro Arg Cys
1 5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Cys Val Ser Asp Pro Arg Cys
1 5

<210> SEQ ID NO 23
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: Xaa1
<222> LOCATION: (1)..(1)
<223> OTHER INFORMATION: Xaa1 is selected from any amino acid or is absent
<220> FEATURE:
<221> NAME/KEY: Xaa2
<222> LOCATION: (2)..(2)
<223> OTHER INFORMATION: Xaa2 is selected from any amino acid residue wherein the side chains of the amino acids form a linker when Xaa2 and Xaa7 are taken together
<220> FEATURE:
<221> NAME/KEY: Xaa5

<222> LOCATION: (5)..(5)
<223> OTHER INFORMATION: Xaa5 is selected from any amino acid
<220> FEATURE:
<221> NAME/KEY: Xaa6
<222> LOCATION: (7)..(7)
<223> OTHER INFORMATION: Xaa6 is selected from any amino acid
<220> FEATURE:
<221> NAME/KEY: Xaa7
<222> LOCATION: (8)..(8)
<223> OTHER INFORMATION: Xaa7 is selected from any amino acid residue wherein the side chains of the amino acids form a linker when Xaa2 and Xaa7 are taken together

<400> SEQUENCE: 23

Xaa Xaa Ser Ser Xaa Pro Xaa Xaa
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Gly Glu Ser Ser Asp Pro Arg Lys
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Gly Asp Ser Ser Asp Pro Arg Lys
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: Xaa
<222> LOCATION: (8)..(8)
<223> OTHER INFORMATION: Xaa denotes ornithine

<400> SEQUENCE: 26

Gly Asp Ser Ser Asp Pro Arg Xaa
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic

<400> SEQUENCE: 27

Gly Cys Ser Ser Asp Pro Arg Ala
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Gly Ala Ser Ser Asp Pro Arg Cys
1 5

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Gly Gly Cys Ser Ser Tyr Pro Pro Cys
1 5

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Gly Cys Ser Ser Asp Pro Arg Cys Ala
1 5

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Gly Cys Ser Ser Asp Pro Arg Cys Trp
1 5

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gly Cys Ser Ser Asp Pro Arg Cys Arg
1 5

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Gly Cys Ser Ser Asp Pro Arg Cys Lys
1 5

<210> SEQ ID NO 34
<211> LENGTH: 9
<212> TYPE: PRT
<213> ORGANISM: Artificial Sequence
<220> FEATURE:

<223> OTHER INFORMATION: Synthetic

<400> SEQUENCE: 34

Gly Cys Ser Ser Asp Pro Arg Cys Asp
1 5

<210> SEQ ID NO 35
<211> LENGTH: 10
<212> TYPE: PRT
<213> ORGANISM: Artificial Sequence
<220> FEATURE:
<223> OTHER INFORMATION: Synthetic

<400> SEQUENCE: 35

Gly Cys Ser Ser Asp Pro Arg Cys Arg Tyr
1 5 10

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Gly Cys Ser Ser Asp Pro Arg Cys Asn Tyr Asp His
1 5 10

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Cys Ser Ser Asp Pro Arg Cys Ser Ser Asp Pro Arg
1 5 10

<210> SEQ ID NO 38
<211> LENGTH: 14
<212> TYPE: PRT
<213> ORGANISM: Artificial Sequence
<220> FEATURE:
<223> OTHER INFORMATION: Synthetic

<400> SEQUENCE: 38

Gly Cys Ser Ser Asp Pro Arg Cys Thr Lys Ser Ile Pro Pro
1 5 10

<210> SEQ ID NO 39
<211> LENGTH: 12
<212> TYPE: PRT
<213> ORGANISM: Artificial Sequence
<220> FEATURE:
<223> OTHER INFORMATION: Synthetic

<400> SEQUENCE: 39

Gly Gly Cys Ser Ser Asp Pro Arg Cys Phe Pro Asp
1 5 10

<210> SEQ ID NO 40
<211> LENGTH: 16
<212> TYPE: PRT
<213> ORGANISM: Artificial Sequence
<220> FEATURE:
<223> OTHER INFORMATION: Synthetic

<400> SEQUENCE: 40

Gly Cys Cys Ser Asp Pro Arg Cys Asn Tyr Asp His Pro Glu Ile Cys
1 5 10 15

<210> SEQ ID NO 41
<211> LENGTH: 16
<212> TYPE: PRT
<213> ORGANISM: Artificial Sequence
<220> FEATURE:
<223> OTHER INFORMATION: Synthetic

<400> SEQUENCE: 41

Gly Gly Cys Cys Ser Tyr Pro Pro Cys Ile Ala Asn Asn Pro Leu Cys
1 5 10 15

<210> SEQ ID NO 42
<211> LENGTH: 16
<212> TYPE: PRT
<213> ORGANISM: Artificial Sequence
<220> FEATURE:
<223> OTHER INFORMATION: Synthetic

<400> SEQUENCE: 42

Gly Cys Cys Ser His Pro Pro Cys Phe Leu Asn Asn Pro Asp Tyr Cys
1 5 10 15

<210> SEQ ID NO 43
<211> LENGTH: 14
<212> TYPE: PRT
<213> ORGANISM: Artificial Sequence
<220> FEATURE:
<223> OTHER INFORMATION: Synthetic

<400> SEQUENCE: 43

Gly Cys Cys Ser Asp Pro Arg Cys Arg Tyr Arg Cys Arg Cys
1 5 10

<210> SEQ ID NO 44
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: Xaa1
<222> LOCATION: (1)..(1)
<223> OTHER INFORMATION: Xaa1 is selected from any amino acid or is absent
<220> FEATURE:
<221> NAME/KEY: Xaa2
<222> LOCATION: (2)..(2)
<223> OTHER INFORMATION: Xaa2 is selected from any amino acid residue wherein the side chains of the amino acids form a linker when Xaa2 and Xaa7 are taken together
<220> FEATURE:
<221> NAME/KEY: Xaa4
<222> LOCATION: (4)..(4)
<223> OTHER INFORMATION: Xaa4 is selected from any amino acid
<220> FEATURE:
<221> NAME/KEY: Xaa5
<222> LOCATION: (5)..(5)
<223> OTHER INFORMATION: Xaa5 is selected from any amino acid
<220> FEATURE:
<221> NAME/KEY: Xaa6
<222> LOCATION: (7)..(7)
<223> OTHER INFORMATION: Xaa6 is selected from any amino acid
<220> FEATURE:
<221> NAME/KEY: Xaa7
<222> LOCATION: (8)..(8)
<223> OTHER INFORMATION: Xaa7 is selected from any amino acid residue -continued wherein the side chains of the amino acids form a linker when Xaa2
and Xaa7 are taken together

<400> SEQUENCE: 44

Xaa Xaa Ser Xaa Xaa Pro Xaa Xaa
1 5

<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45

Cys Arg Pro Asp Ser Ser Cys Gly
1 5

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Gly Cys Ser Ser Asp Pro Arg Cys
1 5

<210> SEQ ID NO 47
<211> LENGTH: 8
<212> TYPE: PRT
<213> ORGANISM: Artificial Sequence
<220> FEATURE:
<223> OTHER INFORMATION: Synthetic

<400> SEQUENCE: 47

Cys Arg Pro Asp Ser Ser Cys Gly
1 5

ALPHA CONOTOXIN PEPTIDES

CROSS REFERENCE TO RELATED APPLICATIONS

This application is the U.S. national phase of International Application No. PCT/AU2017/050135 filed 16 Feb. 2017, which designated the U.S. and claims priority to AU Patent Application No. 2016900528 filed 16 Feb. 2016, the entire contents of each of which are hereby incorporated by reference.

REFERENCE TO SEQUENCE LISTING SUBMITTED ELECTRONICALLY

The content of the electronically submitted sequence listing (Name: 0659_0202_Sequence_Listing.txt; Size: 12.3 kilobytes; and Date of Creation: Jun. 3, 2021) is incorporated herein by reference in its entirety.

FIELD OF INVENTION

The present invention relates to novel alpha conotoxin (α-conotoxin) peptides, their use as pharmacological tools and their use in any indication in which inhibition of nicotinic acetylcholine receptors and/or voltage gated calcium channels may be of benefit, for example in the production of analgesia, in enhancing opiate analgesia, in modulating a drug related effects or behaviour, or in the treatment of neuropathic pain, visceral chronic pain or inflammation. The invention also relates to pharmaceutical compositions comprising these peptides.

BACKGROUND

Conotoxin peptides (conotoxins) typically contain 10 to 40 amino acids joined in a linear sequence. These peptides interfere with neurotransmission by targeting a variety of ion-channels or receptors and are found in the venom of marine snails of the genus Conus (cone snails), who are predators of fish, worms or other molluscs. The venom from any single Conus species may contain more than 100 different peptides.

Conotoxin peptides typically contain four (4) or more cysteine residues, which are bonded in pairs to form either two (2) or more disulfide bonds, respectively. α-Conotoxins, for example, typically have from 10 to 40 amino acids with four characteristic cysteine substitutions and a pattern of disulfide bonds. The pattern of disulfide bonds and the distribution of the cysteine residues mean that α-conotoxins can potentially form three disulfide isomers during oxidative folding, including a globular isomer which comprises disulfide bonds between cysteine residues 1 and 3, and between cysteine residues 2 and 4 (CysI-CysIII and CysII-CysIV); a ribbon isomer which comprises disulfide bonds between cysteine residues 1 and 4 and between cysteine residues 2 and 3 (CysI-CysIV and CysII-CysIII); and a beads isomer which comprises disulphide bonds between cysteine residues 1 and 2 and between cysteine residues 3 and 4 (CysI-CysII and CysIII-CysIV). The native form of α-conotoxins is typically the globular isomer.

Conotoxins are divided into classes on the basis of their known physiological targets. α-Conotoxins are one such class, and these peptides are recognised as neuronal or muscle nicotinic acetylcholine receptors (nAChRs) antagonists. Studies of different α-conotoxins, including both naturally occurring α-conotoxins and synthetic variants, have illustrated that these peptides display varying affinity and selectivity for various receptor subtypes, including receptors other than or in addition to nicotinic acetylcholine receptors such as voltage-gated calcium channels (VGCCs).

An alphabetical nomenclature for subtypes of VGCCs has evolved for distinct classes of $Ca^{2+}$ currents, and these are divided into three main families and a number of subtypes. L-type VGCCs require a strong depolarisation for activation and are the main $Ca^{2+}$ currents recorded in muscle and endocrine cells, where they initiate contraction and secretion. N-type, P/Q-type and R-type VGCCs also require strong depolarisation for activation, but these subtypes are mostly found in neurons, where they initiate neurotransmission. T-type VGCCs are activated by weak depolarisations and are transient, and they are found in a wide variety of cell types.

VGCCs are multi-subunit complexes, which include the large pore-forming $\alpha_1$ subunit. Different calcium channel $\alpha_1$ subunits are found in different subtypes of VGCC. In particular, L-type VGCCs are represented by the $\alpha_{1C}$, $\alpha_{1D}$, $\alpha_{1F}$ and $\alpha_{1S}$ ($Ca_v$1.1-1.4) subunits. P/Q-type, N-type and R-type VGCCs are represented by $\alpha_{1A}$ ($Ca_v$2.1), $\alpha_{1B}$ ($Ca_v$2.2) and $\alpha_{1E}$ ($Ca_v$2.3) subunits, respectively. T-type VGCCs are formed by $\alpha_{1G}$, $\alpha_{1H}$ and $\alpha_{1I}$ subunits ($Ca_v$3.1-3.3, respectively). In the development of therapeutic agents, selectivity for the N-type VGCC over the P/Q-type channel is important as it has been suggested that blockade of P/Q-type channels may lead to death.

In addition to nicotinic acetylcholine receptor activity, some α-conotoxins exhibit selectivity for N-type and/or R-type VGCCs. For example, α-conotoxins Vc1.1 and RgIA have been identified as α9α10 nAChR subtype antagonists, as well as inhibitors of N-type (Cav2.2) and R-type (Cav2.3) calcium channels through the gamma-aminobutyric acid B receptor (also referred to as $GABA_B$ receptor or GABABR). $GABA_B$ receptor agonists have been shown to relieve neuropathic and chronic pain. New α-conotoxins, which exhibit different binding profiles and affinities to different subtypes of VGCCs, may be useful in further defining subtypes of VGCCs.

In addition to their use as research tools, α-conotoxins which modulate the activity of N- or R-type calcium channels are useful as therapeutics. N-type VGCCs play important roles in regulating neuronal excitability and nociceptive transmission and are prominently involved in the transduction of acute and chronic pain perception. These channels represent important drug targets for the management of chronic, visceral and neuropathic pain and have been investigated in the development of new analgesic agents.

In view of the involvement in transduction of pain perception and their potent biological activity, conotoxins have been the subject of pharmacological interest. As noted above, α-conotoxins which target N- or R-type calcium channels may be useful as therapeutics for conditions including in the production of analgesia, in enhancing opiate analgesia, in modulating drug related effects or behaviour, or in the treatment of neuropathic pain, chronic pain, visceral pain, inflammation, convulsions, and alcohol dependence. Accordingly, the compounds of the invention may be useful in any indication where the inhibition of nicotinic acetylcholine receptors, N- or R-type calcium channels, and combinations thereof, may be of benefit.

Recent studies suggest that some α-conotoxins, such as Vc1.1, Vc1.2, RgIA, PeIA and AuIB, modulate N-type calcium channel currents via G-protein-coupled $GABA_B$ receptors. $GABA_B$ receptors are widely distributed in the central and peripheral nervous systems. Baclofen, a selective $GABA_B$ receptor agonist, has been used to treat various neurologic disorders, including spasticity, chronic pain, and alcoholism. However, baclofen causes numerous side effects due to its indiscriminate activation of multiple $GABA_B$ receptor signaling pathways. In contrast, native α-conotoxin Vc1.1, for example, activates a distinct voltage-independent $GABA_B$ receptor-Cav2.2 signaling pathway, ultimately inhibiting Cav2.2 channels. This $GABA_B$ receptor-biased signaling mechanism likely contributes to the superior selectivity and analgesic properties of native Vc1.1.

Accordingly, it is considered that the selective activation of $GABA_B$ receptors and subsequent inhibition of $Ca_v2.2$ (N-type) calcium channels by α-conotoxins may provide and/or modulate analgesic properties. As such, new α-conotoxins have potential utility as highly selective and/or specific therapeutics for various conditions including neuropathic pain, chronic pain, and visceral pain.

Furthermore, the alpha7 nAChR (a7 nAChR) subtype has been implicated in a range of neurological diseases including schizophrenia, bipolar disorder, Alzheimer's and Parkinson's diseases, drug dependence, inflammation. α-conotoxins which target α7 nAChR may also be useful as therapeutics for the treatment of one or more of these conditions.

Other conotoxins that selectively inhibit N-type VGCCs, such as ω-conotoxin MVIIA (also know as Prialt, SNX-111, Ziconotide), have been granted regulatory approval by a number of government bodies worldwide for the treatment of severe chronic pain associated with cancer, AIDS and neuropathies. Significantly, MVIIA does not induce tolerance and it also works in patients who no longer respond to opioid drugs. Recently, an orally available, cyclised form of α-conotoxin Vc1.1 has also been developed.

Despite these advances many of the presently available compounds are not ideal therapeutics. A major limitation of peptide-based molecules as drugs is their relatively short plasma half-life. Rapid proteolytic degradation of peptides reduces the efficacy of many conotoxins in vivo and limits their application in a clinical setting. Furthermore, synthesis of such compounds is rarely straightforward and often results in multiple isomers. Additionally, some conotoxin-derived therapeutics have been known to result in deleterious side effects, such as orthostatic hypotension. Backbone cyclisation to form an amide bond between the N- and C-termini has been applied to several conotoxins. Such cyclic analogues comprising varying oligopeptide N- to C-terminus linkers have exhibited improved stability towards proteolytic degradation in simulated in vivo environments, without sacrificing activity at their pharmacological targets.

Accordingly there exists a need for new therapeutic agents which have one or more of selectivity for N-type, R-type VGCCs and/or α7 nAChR or α9α10 nAChR subtypes, favourable binding and/or reversibility characteristics, and/or which may be useful in the treatment of conditions related to N-type, R-type VGCCs and/or α7 nAChR or α9α10 nAChR subtypes.

SUMMARY

It is recognised that α-conotoxins which modulate the activity of N- or R-type calcium channels may be useful as therapeutics. Some α-conotoxins, such as Vc1.1, Vc1.2, RgIA, PeIA and AuIB, inhibit Cav2.2 channels via $GABA_B$ receptors. Baclofen, a selective $GABA_B$ receptor agonist, has been used to treat various neurologic disorders but causes numerous side effects. Conversely, native α-conotoxin Vc1.1, for example, activates a distinct voltage-independent $GABA_B$ receptor-Cav2.2 signaling pathway and demonstrates superior selectivity and analgesic properties when compared with known $GABA_B$ receptor agonists such as baclofen.

The inventors have surprisingly found that truncated analogues of some α-conotoxins can exhibit biological activity and potency which may be comparable to full-length native peptides. Furthermore, certain truncated analogues of α-conotoxins may address one or more of the abovementioned deficiencies. As such, new α-conotoxins have potential utility as potent, specific and/or selective therapeutics for various conditions including neuropathic pain, chronic pain, and visceral pain.

Of particular interest are truncated analogues of α-conotoxins which, in addition to inhibiting nicotinic acetylcholine receptors, are known to activate voltage-independent $GABA_B$ receptor-Cav2.2 signaling pathways, such as α-conotoxins Vc1.1, Vc1.2, RgIA, PeIA and AuIB, Accordingly, in a first aspect the present invention provides a peptide comprising or consisting of the sequence:

SEQ ID NO: 1

$Xaa_1$ $Xaa_2$ $Xaa_3$ $Xaa_4$ $Xaa_5$ P $Xaa_6$ $Xaa_7$ wherein $Xaa_1$ is selected from any amino acid or is absent;

$Xaa_3$ is selected from any amino acid;

$Xaa_2$ and $Xaa_7$ are each independently an amino acid residue wherein the side chains form a linker when $Xaa_2$ and $Xaa_7$ are taken together, $Xaa_4$ is selected from any amino acid;

$Xaa_5$ is selected from any amino acid, and $Xaa_6$ is selected from any amino acid.

In various embodiments, $Xaa_1$ to $Xaa_7$ are selected from a combination of one or more of the following:

$Xaa_1$ is a small amino acid or is absent;

$Xaa_2$ is selected from a small amino acid, a polar amino acid wherein the side chains of the amino acids form a linker when $Xaa_2$ and $Xaa_7$ are taken together;

$Xaa_3$ is selected from a small amino acid, a polar amino acid, or a non polar amino acid;

$Xaa_4$ is selected from a small amino acid or a polar amino acid;

$Xaa_5$ is selected from a small amino acid or a polar amino acid;

$Xaa_6$ is selected from a small amino acid or a polar amino acid; and $Xaa_7$ is selected from a small amino acid, or a polar amino acid, wherein the side chains of the amino acids form a linker when $Xaa_2$ and $Xaa_7$ are taken together.

In some embodiments, $Xaa_1$ to $Xaa_7$ may be selected from a combination of one or more of the following:

$Xaa_1$ is glycine, alanine or is absent;

$Xaa_2$ is cysteine, alanine, glutamic acid, aspartic acid, lysine, or ornithine wherein the side chains of the amino acids form a linker when $Xaa_2$ and $Xaa_7$ are taken together;

$Xaa_3$ is serine, glutamic acid or valine;

$Xaa_4$ is serine, alanine, arginine, histidine, asparagine, lysine, aspartic acid and threonine;

$Xaa_5$ is alanine, aspartic acid, tyrosine, histidine or asparagine;

$Xaa_6$ is arginine, proline, or alanine; and $Xaa_7$ is cysteine, alanine, glutamic acid, aspartic acid, lysine, or ornithine wherein the side chains of the amino acids form a linker when $Xaa_2$ and $Xaa_7$ are taken together.

In some embodiments, $Xaa_2$ and $Xaa_7$ are each cysteine, wherein the side chains of the cysteine residues form a linker when $Xaa_2$ and $Xaa_7$ are taken together. In preferred embodiments, the linker formed is a disulfide bond.

The peptides of the invention may be useful in the treatment of conditions related to N-type, R-type VGCCs and/or α7 nAChR or α9α10 nAChR subtypes. The invention also relates to pharmaceutical compositions comprising these peptides.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Throughout this specification and the claims which follow, unless the context requires otherwise, the phrase "consisting essentially of", and variations such as "consists essentially of" will be understood to indicate that the recited element(s) is/are essential i.e. necessary elements of the invention. The phrase allows for the presence of other non-recited elements which do not materially affect the characteristics of the invention but excludes additional unspecified elements which would affect the basic and novel characteristics of the invention defined.

DETAILED DESCRIPTION

Figure 1:
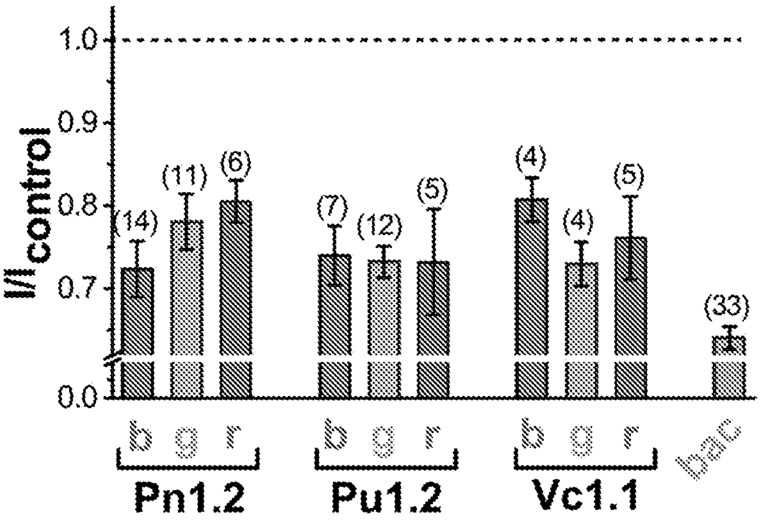
FIG. 1: Activity and/or physicochemical properties of corresponding native full length disulfide isomers of α-conotoxins Pn1.2, Pu1.2 and Vc1.1 in ICa in rat DRG neurons. Beads (blue), globular (green) and ribbon (red). Mean relative peak ICa amplitudes (1/Icontrol)±SEM in the presence of each α-conotoxin (1 μM) are shown. The number of experiments is in parentheses. The specific GABABR agonist baclofen (bac, 50 μM, orange) was used as a positive control. The dotted line indicates maximum current recorded in the absence of α-conotoxin (control).

The present invention relates to truncated analogues of α-conotoxins, including analogues of Vc1.1, which exhibit biological activity and/or potency comparable to the full-length native peptides. The peptides of the invention may be useful in the treatment of conditions related to N-type, R-type VGCCs and/or α7 nAChR or α9α10 nAChR subtypes. The invention also relates to pharmaceutical compositions comprising these peptides.

As described above, in a first aspect of the present invention there is provided a peptide comprising or consisting of the sequence:

SEQ ID NO: 1
$Xaa_1$ $Xaa_2$ $Xaa_3$ $Xaa_4$ $Xaa_5$ P $Xaa_6$ $Xaa_7$ wherein

- $Xaa_1$ is selected from any amino acid or is absent;
- $Xaa_3$ is selected from any amino acid;
- $Xaa_2$ and $Xaa_7$ are each independently an amino acid residue wherein the side chains form a linker when $Xaa_2$ and $Xaa_7$ are taken together,
- $Xaa_4$ is selected from any amino acid;
- $Xaa_5$ is selected from any amino acid, and
- $Xaa_6$ is selected from any amino acid.

In various embodiments, $Xaa_1$ to $Xaa_7$ are selected from a combination of one or more of the following:

- $Xaa_1$ is a small amino acid or is absent;
- $Xaa_2$ is selected from a small amino acid and a polar amino acid wherein the side chains of the amino acids form a linker when $Xaa_2$ and $Xaa_7$ are taken together;
- $Xaa_3$ is selected from a small amino acid, a polar amino acid, and a non polar amino acid;
- $Xaa_4$ is selected from a small amino acid and a polar amino acid;
- $Xaa_5$ is selected from a small amino acid and a polar amino acid;
- $Xaa_6$ is selected from a small amino acid and a polar amino acid; and
- $Xaa_7$ is selected from a small amino acid and a polar amino acid wherein the side chains of the amino acids form a linker when $Xaa_2$ and $Xaa_7$ are taken together.

In some embodiments, $Xaa_1$ to $Xaa_7$ are selected from a combination of one or more of the following:

- $Xaa_1$ is glycine, alanine or is absent;
- $Xaa_2$ is cysteine, alanine, glutamic acid, aspartic acid, lysine, or ornithine wherein the side chains of the amino acids form a linker when $Xaa_2$ and $Xaa_7$ are taken together;
- $Xaa_3$ is serine, glutamic acid or valine;
- $Xaa_4$ is serine, alanine, arginine, histidine, asparagine, lysine, aspartic acid and threonine;
- $Xaa_5$ is alanine, aspartic acid, tyrosine, histidine or asparagine;
- $Xaa_6$ is arginine, proline, or alanine; and
- $Xaa_7$ is cysteine, alanine, glutamic acid, aspartic acid, lysine, or ornithine wherein the side chains of the amino acids form a linker when $Xaa_2$ and $Xaa_7$ are taken together.

In another aspect, wherein $Xaa_3$ is serine, there is provided a peptide comprising or consisting of the sequence:

SEQ ID NO: 44
$Xaa_1$ $Xaa_2$ S $Xaa_4$ $Xaa_5$ P $Xaa_6$ $Xaa_7$ wherein

- $Xaa_1$ is selected from any amino acid or is absent;
- $Xaa_2$ and $Xaa_7$ are independently selected from an amino acid residue wherein the side chains of the amino acids form a linker when $Xaa_2$ and $Xaa_7$ are taken together;
- $Xaa_4$ is selected from any amino acid;
- $Xaa_5$ is selected from any amino acid; and
- $Xaa_6$ is selected from any amino acid.

In some embodiments, $Xaa_2$ and $Xaa_7$ are each cysteine, the side chains of which together form a linker when $Xaa_2$ and $Xaa_7$ are taken together. In preferred embodiments, the linker is a disulfide bond.

The terms "peptide" and "protein" are used herein interchangeably in their broadest sense to refer to oligomers of two or more amino acids, including isolated, synthetic or recombinant peptides. These terms apply to amino acid polymers in which one or more amino acid residues is a synthetic non-naturally-occurring amino acid, such as a chemical analogue of a corresponding naturally-occurring amino acid, as well as to naturally-occurring amino acid polymers. These terms do not exclude modifications, for example, glycosylations, acetylations, phosphorylations and the like. Soluble forms of the subject peptides are particularly useful. Included within the definition are, for example, peptides containing one or more analogues of an amino acid including, for example, unnatural amino acids or peptides with substituted linkages.

The term "amino acid" is used herein in its broadest sense and may refer to compounds having an amino group and a carboxylic acid group. The amino acids incorporated into the peptides of the present invention may be D- or L-forms of proteogenic or naturally occurring amino acids, or may be D- or L-forms of non-proteogenic or non-naturally occurring amino acids. As referred to herein, the term extends to synthetic amino acids and analogues thereof, including salts, isomers, tautomers, esters and N-methylated amino acids.

The terms "selective" and "selectivity" as used herein refers to agents that modulate (e.g. activate) an ion channel subtype of interest without displaying substantial modulation of one or more other ion channel subtypes. Accordingly, by way of example, an agent that is selective for α7 nAChR exhibits α7 nAChR selectivity of greater than about 2-fold, 5-fold, 10-fold, 20-fold, 50-fold or greater than about 100-fold with respect to modulation of one or more other subtypes.

The naturally occurring proteogenic amino acids are shown in Table 1 together with their three letter and one letter codes. L-amino acids are referred to using capital letters or initial capital letters whereas D-amino acids are referred to using lower case letters.

Unless otherwise noted, single letter codes are used herein to denote different amino acids. The naturally occurring proteogenic amino acids are shown in Table 1 together with their three letter and one letter codes. L-amino acids are referred to using capital letters or initial capital letters whereas D-amino acids are referred to using lower case letters

TABLE 1

Codes for conventional amino acids

| Amino acid | L- Three letter code | D- Three letter code | L- One letter code | D- One letter code |
|---|---|---|---|---|
| Alanine | Ala | ala | A | a |
| Arginine | Arg | arg | R | r |
| Asparagine | Asn | asn | N | n |
| Aspartic acid | Asp | asp | D | d |
| Cysteine | Cys | cys | C | c |
| Glutamine | Gln | gln | Q | q |
| Glutamic acid | Glu | glu | E | e |
| Glycine* | Gly | gly | G | g |
| Histidine | His | his | H | h |
| Isoleucine | Ile | ile | I | i |
| Leucine | Leu | leu | L | l |

TABLE 1-continued

| Codes for conventional amino acids | | | | |
|---|---|---|---|---|
| Amino acid | L- Three letter code | D- Three letter code | L- One letter code | D- One letter code |
| Lysine | Lys | lys | K | k |
| Methionine | Met | met | M | m |
| Phenylalanine | Phe | phe | F | f |
| Proline | Pro | pro | P | p |
| Serine | Ser | ser | S | s |
| Threonine | Thr | thr | T | t |
| Tryptophan | Trp | trp | W | w |
| Tyrosine | Tyr | tyr | Y | y |
| Valine | Val | val | V | v |

The amino acid sequence of the peptides useful in the invention may be defined in terms of amino acids of certain characteristics or sub-classes. Amino acid residues are generally sub-classified into major sub-classes, including acidic, basic, charged, hydrophobic or neutral/acidic residues. Acidic residues typically have a negative charge at physiological pH and include amino acids having an acidic side chain such as glutamic acid and aspartic acid. Basic residues typically positive charge s at physiological pH and include amino acids having a basic side chain such as arginine, lysine and histidine. The term “charged residue” encompasses amino acids which are charged at physiological pH and thus includes amino acids having either acidic or basic side chains. Hydrophobic residues tend to be repelled by aqueous environments and are typically found in inner positions in the conformation of a peptide. Such amino acids include hydrophobic side chain such as tyrosine, valine, isoleucine, leucine, methionine, phenylalanine and tryptophan. Unlike hydrophobic residues, neutral/polar residues are not typically repelled by aqueous solutions, and include amino acids having a neutral/polar side chain such as asparagine, glutamine, cysteine, histidine, serine and threonine. Dependent on their structural properties, amino acid residues may fall in two or more classes. For the naturally-occurring protein amino acids, sub-classification according to this scheme is presented in Table 2. Amino acid residues can be further sub-classified as cyclic or non-cyclic, and aromatic or non-aromatic, self-explanatory classifications with respect to the side-chain substituent groups of the residues, and as small or large.

TABLE 2

| Amino Acid Sub-Classification | |
|---|---|
| Sub-classes | Amino Acids |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Nonpolar/neutral | Alanine, Glycine, Isoleucine, Leucine, Methionine, Phenylalanine, Proline, Tryptophan, Valine |
| Polar/neutral | Asparagine, Histidine, Glutamine, Cysteine, Serine, Threonine, Tyrosine |
| Polar/negative | Aspartic acid, Glutamic acid |
| Polar/positive | Lysine, Arginine |
| Polar/large | Asparagine, Glutamine |
| Polar | Arginine, Asparagine, Aspartic acid, Cysteine, Glutamic acid, Glutamine, Histidine, Lysine, Serine, Threonine, Tyrosine |
| Hydrophobic | Tyrosine, Valine, Isoleucine, Leucine, Methionine, Phenylalanine, Tryptophan |

TABLE 2-continued

| Amino Acid Sub-Classification | |
|---|---|
| Sub-classes | Amino Acids |
| Aromatic | Tryptophan, Tyrosine, Phenylalanine |
| Residues that influence chain orientation | Glycine and Proline |

Examples of unnatural or non-proteogenic amino acids include, but are not limited to, use of ornithine, norleucine, 4-amino butyric acid, 4-amino-3-hydroxy-5-phenylpentanoic acid, 6-aminohexanoic acid, t-butylglycine, norvaline, phenylglycine, sarcosine, 4-amino-3-hydroxy-6-methylheptanoic acid and 2-thienyl alanine. Examples of suitable non-proteogenic or non-naturally occurring amino acids contemplated herein is shown in Table 3.

TABLE 3

| Codes for non-conventional amino acids | |
|---|---|
| Non-conventional amino acid | Code |
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |

TABLE 3-continued

Codes for non-conventional amino acids

| Non-conventional amino acid | Code |
|---|---|
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-Nmethylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |

TABLE 3-continued

Codes for non-conventional amino acids

| Non-conventional amino acid | Code |
|---|---|
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |

Unless otherwise specified, the non-proteogenic or non-naturally occurring amino acids listed in Table 3 are in the L-conformation. However, the use of non-proteogenic or non-naturally occurring amino acids having corresponding D-conformations is also envisaged.

It is appreciated that an L-peptide may have three additional corresponding analogue sequences built from L and D amino acids: i) the D-enantiomer or inverso-peptide with the same sequence, but composed of D-amino acids and a mirror conformation; the retro-peptide, consisting of the same sequence of L amino acids but in reverse order; and the retro-inverso or D-retro-enantiomer peptide, consisting of D-amino acids in the reversed sequence. For example, a peptide comprising L-amino acids and having the following sequence, may have three corresponding analogues as outlined below:

| | | |
|---|---|---|
| G C S S D P R C | L-enantiomer | SEQ ID NO: 4 |
| g c s s d p r c | D-enantiomer or inverso-peptide | SEQ ID NO: 46 |
| C R P D S S C G | L-enantiomer retro-peptide | SEQ ID NO: 45 |
| c r p d s s c g | D-retro-inverso-peptide | SEQ ID NO: 47 |

Unless otherwise specified, the peptides referred to herein are in the L-conformation. However, the corresponding D-enantiomer or inverso-peptide, L-enantiomer retro-peptide and D-retro-inverso-peptide are also envisaged.

Disulfide bonds are the primary determinant of conotoxin structure and function, however these bonds are readily reduced in vivo leading to disulfide isomerisation (or "shuffling") which may compromise bioactivity. In an embodiment, the peptides of the present invention may have two cysteine residues. Preferably, the peptides have only two cysteine residues. In a preferred embodiment, the sidechains of the two cysteine residues may together form a disulfide bond. Truncated peptides of SEQ ID No. 1 or 44, which comprise only a single disulfide bond, advantageously provide efficient and/or improved synthesis and the production of only a single disulfide isomer.

Accordingly, in another aspect of the invention, wherein $Xaa_3$ is serine and $Xaa_2$ and $Xaa_7$ are each cysteine, the side chains of which together form a linker, there is provided a peptide which comprises or consists of the following sequence:

SEQ ID NO: 2

$Xaa_1$ C S $Xaa_4$ $Xaa_5$ P $Xaa_6$ C wherein $Xaa_1$ is selected from any amino acid or is absent;

$Xaa_4$ is selected from any amino acid;

$Xaa_5$ is selected from any amino acid; and $Xaa_6$ is selected from any amino acid.

In further aspect of the invention, wherein $Xaa_1$ is glycine, $Xaa_3$ is serine and $Xaa_2$ and $Xaa_7$ are each cysteine, the side chains of which together form a linker, there is provided a peptide which comprises or consists of the following sequence:

SEQ ID NO: 3

G C S $Xaa_4$ $Xaa_5$ P $Xaa_6$ C wherein $Xaa_4$ is selected from any amino acid;

$Xaa_5$ is selected from any amino acid; and $Xaa_6$ is selected from any amino acid.

In some embodiments, wherein the peptide is a peptide of SEQ ID NO. 3, $Xaa_4$, $Xaa_5$ and $Xaa_6$ are each independently selected from a small amino acid or a polar amino acid. In some embodiments, $Xaa_4$ is selected from serine, alanine, lysine, asparagine, threonine, histidine and aspartic acid. In still other embodiments, $Xaa_5$ is selected from alanine, aspartic acid, tyrosine, histidine and asparagine. In other embodiments, $Xaa_6$ is arginine, proline, and alanine.

Representative peptides of SEQ ID NO: 3 include but are not limited to:

| Designated name | SEQ ID NO. | Sequence |
|---|---|---|
| [$Ser^3$]Vc1.1(1-8) | SEQ ID NO: 4 | G C S S D P R C |
| [$Ser^3$,$Ala^4$]Vc1.1(1-8) or [S4A]Vc1.1(1-8) | SEQ ID NO: 5 | G C S A D P R C |
| [$Ser^3$,$Lys^4$]Vc1.1(1-8) or [S4K]Vc1.1(1-8) | SEQ ID NO: 6 | G C S K D P R C |
| [$Ser^3$,$Asn^4$]Vc1.1(1-8) OR [S4N]Vc1.1(1-8) | SEQ ID NO: 7 | G C S N D P R C |
| [$Ser^3$,$Thr^4$]Vc1.1(1-8) or [S4T]Vc1.1(1-8) | SEQ ID NO: 8 | G C S T D P R C |
| [$Ser^3$,$His^4$]Vc1.1(1-8) or [S4H]Vc1.1(1-8) | SEQ ID NO: 9 | G C S H D P R C |
| [$Ser^3$,$Arg^4$]Vc1.1(1-8) or [S4R]Vc1.1(1-8) | SEQ ID NO: 10 | G C S R D P R C |
| [$Ser^3$,$Ala^5$]Vc1.1(1-8) or [D5A]Vc1.1(1-8) | SEQ ID NO: 11 | G C S S A P R C |
| [$Ser^3$,$Ala^7$]Vc1.1(1-8) or [R7A]Vc1.1(1-8) | SEQ ID NO: 12 | G C S S D P A C |
| [$Ser^3$]Vc1.2(1-8) or [C3S]Vc1.2(1-8) | SEQ ID NO: 13 | G C S S N P A C |
| [$Ser^3$]RgIA(1-8) or [C3S]RgIA(1-8) | SEQ ID NO: 14 | G C S S D P R C |
| [$Ser^3$]PeIA(1-8) or [C3S]PeIA(1-8) | SEQ ID NO: 15 | G C S S H P A C |
| [$Ser^3$]AuIB(1-8) or [C3S]Au1B(1-8) | SEQ ID NO: 16 | G C S S Y P P C |

In another aspect of the invention, wherein $Xaa_2$ and $Xaa_7$ are each cysteine, the side chains of which together form a linker, and $Xaa_3$ and $Xaa_4$ are each serine, there is provided a peptide comprising or consisting of the following sequence:

SEQ ID NO: 17
$Xaa_1$ C S S $Xaa_5$ P $Xaa_6$ C wherein $Xaa_1$ is selected from any amino acid or is absent;

$Xaa_5$ is selected from any amino acid; and $Xaa_6$ is selected from any amino acid.

In some embodiments, wherein the peptide is a peptide of SEQ ID NO. 17, $Xaa_1$ is a small amino acid or is absent, and $Xaa_5$ and $Xaa_6$ are each independently selected from a small amino acid or a polar amino acid. In some embodiments, $Xaa_1$ is selected from glycine and alanine or is absent. In other embodiments, $Xaa_5$ is selected from alanine, aspartic acid, tyrosine, histidine and asparagine. In yet further embodiments, $Xaa_6$ is selected from arginine, proline and alanine.

In addition to the examples listed above, other representative peptides of SEQ ID NO: 17 include but are not limited to:

| Designated Name | SEQ ID No. | Sequence |
|---|---|---|
| [Ala$^1$,Ser$^3$]Vc1.1 (1-8) or [G1A]Vc1.1(1-8) | SEQ ID NO: 18 | A C S S D P R C |
| [Ser$^3$]Vc1.1(2-8) or Vc1.1(2-8) | SEQ ID NO: 19 | C S S D P R C |

In further aspect of the invention, wherein $Xaa_1$ is glycine, $Xaa_2$ and $Xaa_7$ are each cysteine, the side chains of which together form a linker, and $Xaa_4$ is serine, there is provided a peptide which comprises or consists of the following sequence:

SEQ ID NO: 20
G C $Xaa_3$ S $Xaa_5$ P $Xaa_6$ C wherein $Xaa_3$ is selected from any amino acid;

$Xaa_5$ is selected from any amino acid; and $Xaa_6$ is selected from any amino acid.

In some embodiments, wherein the peptide is a peptide of SEQ ID NO. 20, $Xaa_3$ is selected from is selected from a small amino acid, a polar amino acid, or a non polar amino acid and $Xaa_5$ and $Xaa_6$ are each independently selected from a small amino acid or a polar amino acid. In some embodiments, $Xaa_3$ is selected from serine, glutamic acid and valine. In still other embodiments, $Xaa_5$ is selected from alanine, aspartic acid, tyrosine, histidine and asparagine. In other embodiments, $Xaa_6$ is arginine, proline, and alanine.

In addition to the examples listed above, other representative peptides of SEQ ID NO: 20 include but are not limited to:

| Designated Name | SEQ ID No. | Sequence |
|---|---|---|
| [Asp$^3$]Vc1.1(1-8) or [S3D]Vc1.1(1-8) | SEQ ID NO: 21 | G C D S D P R C |

-continued

| Designated Name | SEQ ID No. | Sequence |
|---|---|---|
| [Val$^3$]Vc1.1(1-8) or [S3V]Vc1.1(1-8) | SEQ ID NO: 22 | G C V S D P R C |

In another aspect, two or more cysteine residues may be replaced by amino acid residues or functional groups which are bonded in pairs to form a linker. The linker may be any suitable linker. In one embodiment, the linker may be a linker which mimics the physicochemical structure and/or biological activity of a disulfide bond between two cysteine residues in the native peptide. The linker may, for example, provide improved or enhanced stability, physicochemical properties, biological or therapeutic activity when compared with the native peptide. The linker may be selected from any appropriate linker known in the art, including peptidic linkers and non-peptidic linkers.

Accordingly, in another aspect of the invention there is provided a peptide comprising or consisting of the following sequence:

SEQ ID NO: 23
$Xaa_1$ $Xaa_2$ S S $Xaa_5$ P $Xaa_6$ $Xaa_7$.

wherein $Xaa_1$ is selected from any amino acid or is absent;

$Xaa_2$ and $Xaa_7$ are selected from amino acid residues wherein the side chains of the amino acids form a linker when $Xaa_2$ and $Xaa_7$ are taken together;

$Xaa_5$ is selected from any amino acid; and $Xaa_6$ is selected from any amino acid.

In some embodiments, $Xaa_2$ and $Xaa_7$ are each cysteine, the side chains of which together form a linker. In preferred embodiments, the linker is a disulfide bond.

In other embodiments, the linker is a linker which mimics the physicochemical structure and/or biological activity of a disulfide bond between two cysteine residues, such a linker may, for example, comprise a multivalent group that covalently links two amino acids in the peptide backbone. In particular embodiments, the linker may be formed at least in part, from the functional side chains of one or more amino acids residues in the peptide backbone.

The term "side chain" or "functional side chain" is used in the usual sense to refer to the side chain on the amino acid, and the backbone to the $H_2N—(C)_x—CO_2H$ (where x=1, 2 or 3) component, in which the carbon in bold text bears the side chain (the side chain being possibly linked to the amino nitrogen, as in the case of proline). The "amino acid(s)" and "amino acid residue(s)" may be used interchangeably herein.

In an embodiment, the or each linking group is a multivalent form of a group selected from alkyl, alkenyl, alkynyl, aryl, acyl, carbocyclyl, heteroalkyl, heteroalkenyl, heteroalkynyl, heterocyclyl, heteroaryl, alkyloxy, alkenyloxy, alkynyloxy, aryloxy, acyloxy, carbocyclyloxy, heterocyclyloxy, heteroaryloxy, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio.

In an embodiment, the or each linking group is a multivalent form of a group selected from $C_1$-$C_{12}$ alkyl, $C_2$-$C_{12}$ alkenyl, $C_2$-$C_{12}$ alkynyl, $C_5$-$C_{18}$ aryl, $C_1$-$C_{12}$ heteroalkyl, $C_3$-$C_{18}$ heteroaryl, $C_3$-$C_{18}$ carbocyclyl, $C_1$-$C_{12}$ heteroalkyl $C_2$-$C_{18}$ heterocyclyl, $C_6$-$C_{18}$ alkylaryl, $C_4$-$C_{18}$alkylheteroaryl, $C_4$-$C_{18}$ alkylcarbocyclyl, and $C_3$-$C_{18}$ alkylheterocyclyl $C_1$-$C_{18}$ alkyloxy, $C_2$-$C_{18}$ alkenyloxy, $C_2$-$C_{18}$ alkynyloxy, acyl, acyloxy, $C_1$-$C_{18}$ alkylthio, $C_2$-$C_{18}$ alkenylthio, $C_2$-$C_{18}$ alkynylthio, $C_5$-$C_{18}$ arylthio, acylthio, sulfonyl, sulfoxyl, $C_1$-$C_{18}$ alkylamino, $C_2$-$C_{18}$ alkenylamino, $C_2$-$C_{18}$ alkynylamino, $C_5$-$C_{18}$ arylamino, and acylamino.

In an embodiment, the or each linking group is a multivalent form of a group selected from $C_1$-$C_{12}$ alkyl, $C_2$-$C_{12}$ alkenyl, $C_2$-$C_{12}$ alkynyl, $C_5$-$C_{18}$ aryl, $C_1$-$C_{12}$ heteroalkyl, $C_3$-$C_{18}$ heteroaryl, $C_3$-$C_{18}$ carbocyclyl, $C_1$-$C_{12}$ heteroalkyl $C_2$-$C_{18}$ heterocyclyl, $C_6$-$C_{18}$ alkylaryl, $C_4$-$C_{18}$ alkylheteroaryl, $C_4$-$C_{18}$ alkylcarbocyclyl, and $C_3$-$C_{18}$ alkylheterocyclyl $C_1$-$C_{18}$ alkyloxy, $C_2$-$C_{18}$ alkenyloxy, $C_2$-$C_{18}$ alkynyloxy, acyl, acyloxy, $C_1$-$C_{18}$ alkylthio, $C_2$-$C_{18}$ alkenylthio, $C_2$-$C_{18}$ alkynylthio, $C_5$-$C_{18}$ arylthio, acylthio, sulfonyl, sulfoxyl, $C_1$-$C_{18}$ alkylamino, $C_2$-$C_{18}$ alkenylamino, $C_2$-$C_{18}$ alkynylamino, $C_5$-$C_{18}$ arylamino, and acylamino.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, hydroxyl, acyl, amino, alkyl, alkenyl, alkynyl, aryl, alkoxy, alkylamino, alkenylamino, alkylheterocyclyl, cycloalkyl, cycloalkenyl, cycloalkylamino, cycloalkenylamino, arylamino, heteroaryl, heterocyclyl, heteroarylamino, heterocyclylamino, aminoarylamino, aminoheteroarylamino, aminoheterocyclylamino, tetrahydropyridinylamino, azetidinyl, pyrrolidinyl, piperidinyl, piperazinyl, morpholinyl, azetidinylamino, pyrrolidinylamino, piperidinylamino, piperazinylamino, azetidinylcarbonylamino, pyrrolidinylcarbonylamino, piperidinylcarbonylamino, piperazinylcarbonylamino, alkoxy, alkenyloxy, alkynyloxy, cycloalkoxy, cycloalkenyloxy, aryloxy, heteroaryloxy, heterocyclyloxy, aminoalkoxy, aminoalkenyloxy, aminoalkynyloxy, aminocycloalkoxy, aminocycloalkenyloxy, aminoaryloxy, aminoheteroaryloxy, azetidinyloxy, pyrrolidinyloxy, piperidinyloxy, or piperazinyloxy.

"Acyl" refers to an R—C(=O)— group in which the R group may be an alkyl, cycloalkyl, heterocycloalkyl, aryl or heteroaryl group as defined herein. Examples of acyl include acetyl and benzoyl.

"Alkyl" as a group or part of a group refers to a straight or branched aliphatic hydrocarbon group, including a $C_1$-$C_{18}$ alkyl, including a $C_1$-$C_{18}$ alkyl, and including $C_1$-$C_6$ alkyl unless otherwise noted.

"Alkylene" refers to divalent alkyl groups having from 1 to 10 carbon atoms including from 1 to 6 carbon atoms, and including 1 to 3 carbon atoms. Examples of such alkylene groups include methylene ($—CH_2—$), ethylene ($—CH_2CH_2—$), and the propylene isomers (e.g., $—CH_2CH_2CH_2—$ and $—CH(CH_3)CH_2—$), and the like.

"Alkenyl" refers to an aliphatic hydrocarbon group containing at least one carbon-carbon double bond and which may be straight or branched, including a $C_2$-$C_{10}$ alkenyl, including a $C_2$-$C_8$ alkenyl, including preferably $C_2$-$C_6$ alkenyl. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl.

"Alkynyl" refers to an aliphatic hydrocarbon group containing a carbon-carbon triple bond and which may be straight or branched, including a $C_2$-$C_{10}$alkynyl, including a $C_2$-$C_8$alkynyl, including $C_2$-$C_6$alkynyl.

"Alkoxy" as a group or part of a group refers to an alkyl-O— group in which alkyl is as defined herein. In an embodiment the alkoxy is a $C_1$-$C_{10}$alkoxy. Examples include, but are not limited to, methoxy and ethoxy.

"Aryl" refers to an unsaturated aromatic carbocyclic group having a single ring (eg., phenyl) or multiple condensed rings (eg., naphthyl or anthryl), including from 6 to 14 carbon atoms. Examples of aryl groups include phenyl, naphthyl and the like.

"Aryloxy" refers to an aryl-O— group in which the aryl is as defined herein. In an embodiment, the aryloxy is a $C_6$-$C_{10}$aryloxy.

"Cycloalkyl" refers to a saturated monocyclic or fused or Spiro polycyclic, carbocycle including from 3 to 10 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane.

"Cycloalkenyl" refers to a non-aromatic monocyclic or multicyclic ring system containing at least one carbon-carbon double bond and including from 5-10 carbon atoms per ring. Exemplary monocyclic cycloalkenyl rings include cyclopentenyl, cyclohexenyl or cycloheptenyl.

"Cycloalkoxy" refers to a cycloalkyl-O— group in which cycloalkyl is as defined herein. In an embodiment, the cycloalkoxy is a $C_3$-$C_{10}$cycloalkoxy. Examples include, but are not limited to, cyclopropanoxy and cyclobutanoxy.

"Heteroalkyl" as a group or part of a group refers to a straight or branched aliphatic hydrocarbon group, including a $C_1$-$C_{10}$ heteroalkyl, including a $C_1$-$C_8$heteroalkyl, including $C_1$-$C_6$ heteroalkyl unless otherwise noted, wherein one or more carbons in the aliphatic chain has been replaced by a heteroatom selected from S, O, P and N. Exemplary heteroalkyls include alkyl ethers, secondary and tertiary alkyl amines, amides, alkyl sulfides, and the like.

"Heteroalkenyl" refers to an aliphatic hydrocarbon group containing at least one carbon-carbon double bond and which may be straight or branched, including a $C_2$-$C_{10}$alkenyl, including a $C_2$-$C_8$ heteroalkenyl, including a $C_2$-$C_6$ heteroalkenyl, wherein one or more carbons in the aliphatic chain has been replaced by a heteroatom selected from S, O, P and N. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl.

"Heteroalkynyl" refers to an aliphatic hydrocarbon group containing a carbon-carbon triple bond and which may be straight or branched, including a $C_2$-$C_{10}$heteroalkynyl, including a $C_2$-$C_8$ heteroalkynyl, including a $C_2$-$C_6$heteroalkynyl, wherein one or more carbons in the aliphatic chain has been replaced by a heteroatom selected from S, O, P and N.

"Heteroaryl" either alone or part of a group refers to groups containing an aromatic ring (including a 5, 6, 9, 10 or 11 membered aromatic ring) having one or more heteroatoms as ring atoms in the aromatic ring with the remainder of the ring atoms being carbon atoms. Suitable heteroatoms include nitrogen, oxygen and sulphur. Examples of a heteroaryl group include triazole, thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl, and includes benzofused heteroaryl, such as benzothiophene, benzofuran, benzimidazole, benzoxazole, benzothiazole, benzisothiazole, and naphtho[2,3-b]thiophene.

"Heterocyclyl" or "heterocyclic" refers to a saturated monocyclic, bicyclic, or polycyclic ring containing at least one heteroatom selected from nitrogen, sulfur, oxygen, including from 1 to 3 heteroatoms in at least one ring. Each ring including from 3 to 11 membered rings, including 4 to 7 membered rings and 9 to 11 membered rings. Examples of suitable heterocyclyl substituents include aziridinyl, oxiranyl, thiiranyl, azetidinyl, oxetanyl, thistanyl, pyrrolinyl, pyrrolidinyl, pyrazolidinyl, imidazolidinyl, tetrahydrofuryl, tetrahydrothiofuranyl, piperidinyl, thiazolidinyl, piperazinyl, tetrahydropyridinyl, morpholino, thiomorpholinyl, 1,3-diazapane, 1,4-diazapane, 1,4-oxazepane, and 1,4-oxathiapane, and includes benzofused compounds such as inddinyl, isoindolinyl, oxoisoindolinyl, isoquinolinyl, and quinolinyl.

The terms "dicarba", "dicarba bond" or "dicarba linker" are used interchangeably and refer to where two amino acid residues both having a side chain double bond are reacted with one another to result in covalent bonding between a carbon atom from each side chain to form a —CH═CH— or —$CH_2$—$CH_2$— bond. In particular embodiments, the covalent bond is formed by ring closing metathesis to form a —CH═CH— bond which may then be optionally reduced to provide a single bond, —$CH_2$—$CH_2$—.

In an embodiment, the or each linking group is a multivalent form of a group selected from a bond, a disulfide linker, an amide linker, a thioether linker, a thiol linker, an acylthio linker, an ester linker, an alkyl linker, an alkenyl linker and an alkynyl linker.

In one embodiment, wherein the linker is a linker which mimics the physicochemical structure and/or biological activity of a disulfide bond between two cysteine residues, the linker may comprise an amide moiety. For example, one or more cysteine residues may be replaced by amino acid residues to form a loop comprising an amide bond which mimics the structure of a disulfide bond. Accordingly, in an embodiment, $Xaa_2$ and $Xaa_7$ are independently selected from amino acid residues which comprise functional group side chains having a carboxyl or amino group. In one embodiment, when $Xaa_2$ has a functional group side chain comprising an amino group, $Xaa_7$ will have a functional group side chain comprising a carboxyl group. In still another embodiment, $Xaa_2$ and $Xaa_7$ may comprise the inverse functional side chains. For example, $Xaa_2$ may include a functional group side chain comprising an carboxyl group and $Xaa_7$ may include a functional group side chain comprising a carboxyl group. When take together, $Xaa_2$ and $Xaa_7$ may form a loop or bond comprising an amide which mimics a disulfide bond between two cysteine residues.

In one embodiment, when $Xaa_2$ is selected from glutamic acid and aspartic acid, $Xaa_7$ may be selected from lysine, histadine, ornithine, and diaminobutyric acid. In still other embodiments, when $Xaa_2$ is selected from lysine, histadine, ornithine, and diaminobutyric acid, $Xaa_7$ may be selected from glutamic acid and aspartic acid.

Accordingly, when $Xaa_2$ is glutamic acid and $Xaa_7$ is lysine in the peptide of SEQ ID No. 23, there is provided a peptide designated as Vc1.1(1-8)amide 8-membered, which comprises or consists of the sequence:

SEQ ID NO: 24
G E S S D P R K wherein the side chains of glutamic acid and lysine residues $Xaa_2$ and $Xaa_7$ together form an amide linker.

Further, when $Xaa_2$ is aspartic acid and $Xaa_7$ is lysine in the peptide of SEQ ID No. 23, there is provided a peptide designated as Vc1.1(1-8)amide 7-membered, which comprises or consists of the sequence:

SEQ ID NO: 25
G D S S D P R K wherein the side chains of aspartic acid and lysine residues $Xaa_2$ and $Xaa_7$ together form an amide linker.

Further, when $Xaa_2$ is aspartic acid and $Xaa_7$ is ornithine in the peptide of SEQ ID No. 23 there is provided a peptide designated as Vc1.1(1-8)amide 6-membered, which comprises or consists of the sequence:

SEQ ID NO: 26
G D S S D P R X wherein the side chains of aspartic acid and ornithine residues $Xaa_2$ and $Xaa_7$ together form an amide linker. Note, X in SEQ ID NO: 26 denotes ornithine.

In another embodiment, wherein the linker is a linker which mimics the physicochemical structure and/or biological activity of a disulfide bond between two cysteine residues, the linker may comprise an acyl linker. Acyl linkers may be formed by any appropriate method known in the art.

In one embodiment, wherein the linker is a linker which mimics the physicochemical structure and/or biological activity of a disulfide bond between two cysteine residues, the linker may comprise an acylthio linker. For example, when $Xaa_2$ and $Xaa_7$ are each cysteine and the cysteine residues are together linked by an acyl group, such as an acetone linker, there is provided peptide designated as Vc1.1(1-8)DCA, which comprises or consists of the following formula:

Vc1.1(1-8)DCA

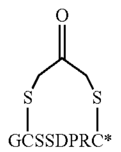

In another embodiment, where the linker comprises a linker which mimics the physicochemical structure and/or biological activity of a disulfide bond between two cysteine residues may comprise a heteroalkyl linker. Heteroalkyl linkers may be formed by any appropriate method known in the art. In one embodiment, the heteroalkyl linker is an alkyl ether or an alkyl thioether.

For example, when $Xaa_2$ is cysteine and $Xaa_7$ is alanine and wherein the functional side chains together form an alkyl thioether, there is provided an isolated, synthetic or recombinant peptide or a derivative thereof designated as Vc1.1(1-8)thioether (1), which comprises or consists of the sequence:

SEQ ID NO: 27
G C S S D P R A

Alternatively, when $Xaa_2$ is alanine and $Xaa_7$ is cysteine and wherein the functional side chains together form an alkyl thioether, there is provided an isolated, synthetic or recombinant peptide or a derivative thereof designated as Vc1.1(1-8)thioether (2), which comprises or consists of the sequence:

SEQ ID NO: 28
G A S S D P R C

In another embodiment, one or more cysteine residues may be replaced with selenocysteine. In this embodiment, the sulphydryl groups of cysteine are replaced with selenium equivalents. The presence of two selenocysteine residues in a peptide chain allows the formation of a diselenide bond which is analogous to the disulfide bond. Disulfides and diselenides both exhibit similar bond geometry, with a diselenide exhibiting a slightly longer bond length due to the larger size of the selenium atom.

Advantageously, in some embodiments, the peptides of the present invention may not include methionine. Methionine residues are prone to oxidation, which can result in reduced purity, and loss of activity or selectivity in solution. This can pose particular problems in terms of storing the peptide over a long period of time, as is the case for formulated peptides delivered from a reservoir of a pumping device.

Despite the difference in chemical properties, substitution of cysteine with selenocysteine represents one of the most conservative substitutions that can be introduced into a peptide, since both exhibit very similar physical properties. The presence of two selenocysteine residues in a peptide chain allows the formation of a diselenide bond which is analogous to the disulfide bond. Disulfides and diselenides both exhibit similar bond geometry, with a diselenide exhibiting a slightly longer bond length due to the larger size of the selenium atom. Methods of preparing selenocysteine would be known to a person skilled in the art.

In another embodiment, wherein the linker is a linker which mimics the physicochemical structure and/or biological activity of a disulfide bond between two cysteine residues, the linker may be selected from an alkyl linker, an alkenyl linker or an alkynyl linker. In one or more embodiments wherein the linker is selected from an alkyl linker, an alkenyl linker or an alkynyl linker, the linker may be referred to as a "dicarba linker" or "dicarba bond". In some embodiments, the wherein the linker is a dicarba linker, the linker may comprise one or more covalent bonds between a carbon atom from the side chain of two or more amino acids, to form a $-CH{=}CH-$ or $-CH_2-CH_2-$ bond.

In some embodiments, wherein the linker is a dicarba bond, $Xaa_2$ and $Xaa_7$ are both allylglycine residues and the dicarba bond is a double bond formed by ring closing metathesis between the double bonds of the allyl groups.

Substitution of disulfides with a linker may affect the properties of the compounds of the present invention. For instance, some linkers may exhibit increased stability in a reducing environment, such as the cytosol. As the mode of action of many drugs often occurs in a reducing environment, systematic replacement of cysteine with amino acids which form an alternative linker may result in increased stability.

In another aspect, there is provided peptides comprising non-natural or non-proteogenic amino acids. In one embodiment, there is provided a retro-inverso or D-retro-enantiomer peptide, consisting of D-amino acids in the reversed sequence. For example, the peptide Vc1.1(1-8) comprising L-amino acids may have a D-retro-enantiomer which comprises or consists of the following sequence:

SEQ ID NO: 47
c r p d s s c g
D-retro-inverso-peptide

One or more amino acids or other substituents may be added to the N- or C-termini of the peptides of the present invention. For example, the peptides of the present invention may form part of a longer sequence with one or more additional amino acids added to either or both of the N- and C-termini. In some embodiments, the peptide or a derivative thereof comprises one or more additional amino acids at the N-terminus. In one embodiment, the peptide or a derivative thereof comprises an additional amino acid at the N-terminus, such as, an additional glycine residue. When the peptide comprises an additional glycine residue at the N-terminus, and $Xaa_1$ is glycine, $Xaa_2$ and $Xaa_7$ are each cysteine, the side chains of which together form a linker, $Xaa_3$ and $Xaa_4$ are each serine, $Xaa_5$ is tyrosine and $Xaa_6$ is proline, there is provided an isolated, synthetic or recombinant peptide or a derivative thereof designated as [$Ser^4$]Pu1.2(1-9) or [C4S] Pu1.2 which comprises or consists of the sequence:

SEQ ID NO: 29
G G C S S Y P P C

In other embodiments, the peptide or a derivative thereof comprise one or more additional amino acids at the C-terminus. In one embodiment, the peptide or a derivative thereof comprises one additional amino acid at the C-terminus, such as an additional alanine, an additional tryptophan, an additional arginine, an additional lysine or an additional aspartic acid residue at the C-terminus. In still another embodiment, the peptide or a derivative thereof comprises two additional amino acids at the C-terminus, such as, an additional arginine and additional tyrosine. In a further embodiment, the peptide or a derivative thereof comprises three additional amino acids at the C-terminus. In yet another embodiment, the peptide or a derivative thereof comprises four additional amino acids at the C-terminus, such as additional asparagine, tyrosine, aspartic acid and histidine residues at the C-terminus.

Representative examples include but are not limited to:

| Designated names | SEQ ID No. | Sequence |
|---|---|---|
| [$Ser^3$, $Ala^9$] Vc1.1(1-9) | SEQ ID NO: 30 | G C S S D P R C A |
| [$Ser^3$, $Trp^9$] Vc1.1(1-9) | SEQ ID NO: 31 | G C S S D P R C W |
| [$Ser^3$, $Arg^9$] Vc1.1(1-9) | SEQ ID NO: 32 | G C S S D P R C R |
| [$Ser^3$, $Lys^9$] Vc1.1(1-9) | SEQ ID NO: 33 | G C S S D P R C K |
| [$Ser^3$, $Asp^9$] Vc1.1(1-9) | SEQ ID NO: 34 | G C S S D P R C D |
| RgIA(1-10) | SEQ ID NO: 35 | G C S S D P R C R Y |
| [$Ser^3$] Vc1.1(1-12) | SEQ ID NO: 36 | G C S S D P R C N Y D H |

Other examples of peptides comprising additional amino acids include but are not limited to a peptide which comprises or consists of one of the following formulae:

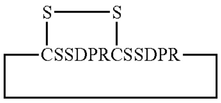

c(Vcl.1(2-8))$_2$

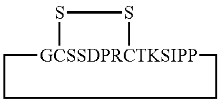

SFTI-1(Vcl.1(1-8))A

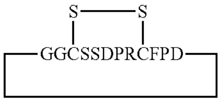

SFTI-1(Vcl.1(1-8))B

In another example, various non-peptidic substituents may also be added to either or both of the N- and C-termini. Since such additional substituents do not necessarily bind to or occlude the primary target of the peptides of the present invention, the N- and C-termini may be modified to alter physicochemical properties, potentially reduce any side effects, or otherwise improve the therapeutic use of the peptide, such as by improving stability. In one example, modifications at the N- or C-termini may improve membrane penetration or solubility.

In one embodiment, a primary, secondary or tertiary amide or an ester may be present at the C-terminus of the peptides of the present invention. The peptides are amidated or have a free carboxyl group at the C-terminus. In further embodiments, the peptides comprise a primary amide or a free carboxyl group at the C-terminus. In still other embodiments, the peptides comprise a primary amide at the C-terminus.

Similarly, compounds with a substituted amine or substituted amide at the N-terminus are also considered to be within the scope of the present invention. In further embodiments, the N-terminus of the peptide is a primary amine, pyroglutamide or acetamide. In still other embodiments, the N-terminus of the peptide is a primary amine.

In one embodiment, the C-terminus of the peptide is a primary amide and the N-terminus is unsubstituted.

The peptides of the present invention may also be attached to a solid support. This may be achieved by linking the sequence to the support via either the N- or C-termini. Various linkers, including peptidic linkers, may used to link the sequence to the solid support.

In a further embodiment, the C-terminus of the conotoxin peptide may be further linked to the N-terminus. The N- and C-termini would generally be linked via a linking moiety, although in some cases it may be possible to directly connect the N- and C-termini of the conotoxin peptide without the need for such a linking moiety. The linking moiety, if present, may be a peptide linker such that cyclisation produces an amide-cyclised peptide backbone. These peptides will have no free N- or C-termini.

Examples of peptides comprising an amide-cyclised peptide backbone include, but are not limited to a peptide which comprises or consists of the following sequences:

SEQ ID NO: 37
C S S D P R C S S D P R

SEQ ID NO: 38
G C S S D P R C T K S I P P

SEQ ID NO: 39
G G C S S D P R C F P D

In certain embodiments, wherein the side chains of the cysteines at $Xaa_2$ and $Xaa_7$ of a peptide of SEQ ID Nos. 37, 38 or 39 together form a disulfide bond, the respective peptides may have the following formulae:

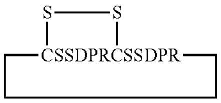

c(Vcl.1(2-8))$_2$

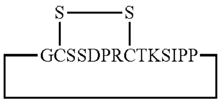

SFTI-1(Vcl.1(1-8))A

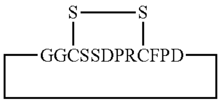

SFTI-1(Vcl.1(1-8))B

Considerable variation in the peptide sequence of this linking moiety is possible. Since this linking region does not necessarily bind to or occlude the primary active site of the peptides of the invention, the linking region can be modified to alter physiochemical properties, and potentially reduce side effects of the peptides, or otherwise improve the therapeutic use of the peptides, such as by improving stability.

The linking moiety will necessarily be of sufficient length to span the distance between the N- and C-termini of the conotoxin peptide. In the case of peptide linkers the length will generally be in the order of 2 to 10 amino acids. In some cases longer or shorter peptide linkers may be required. In one example, the linking moiety may be composed of glycine and/or alanine residues in addition to any amino acid residues already present in the linear peptide.

Therefore, according to one embodiment of the peptides of the present invention, the C-terminus of the peptide is a carboxyl group or a primary amide, or the C-terminus is linked to the N-terminus by a linker.

With respect to the compounds disclosed herein the following combinations of any one or more of (i) to (vii) are contemplated:

i) $Xaa_1$ is glycine; or
   $Xaa_1$ is alanine; or
   $Xaa_1$ is absent.
ii) $Xaa_2$ is cysteine; or
   $Xaa_2$ is alanine; or
   $Xaa_2$ is glutamic acid; or
   $Xaa_2$ is aspartic acid.
iii) $Xaa_3$ is serine; or
   $Xaa_3$ is aspartic acid; or
   $Xaa_3$ is valine.
iv) $Xaa_4$ is serine; or
   $Xaa_4$ is alanine; or
   $Xaa_4$ is lysine, or
   $Xaa_4$ is asparagine, or
   $Xaa_4$ is threonine, or
   $Xaa_4$ is histidine, or
   $Xaa_4$ is arginine.
v) $Xaa_5$ is aspartic acid; or
   $Xaa_5$ is tyrosine; or
   $Xaa_5$ is asparagine; or
   $Xaa_5$ is histidine.
vi) $Xaa_6$ is arginine; or
   $Xaa_6$ is proline; or
   $Xaa_6$ is alanine.
vii) $Xaa_7$ is cysteine; or
   $Xaa_7$ is alanine; or
   $Xaa_7$ is lysine; or
   $Xaa_7$ is ornithine.

Representative examples of compounds of the invention include:

| Designated name | SEQ ID NO. | Sequence | Structure |
|---|---|---|---|
| [$Ser^3$]Vc1.1(1-8) | SEQ ID No. 4 | G C S S D P R C | 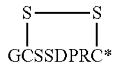 |
| [$Ala^1$,$Ser^3$]Vc1.1(1-8) or [G1A]Vc1.1(1-8) | SEQ ID No. 18 | A C S S D P R C | 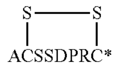 |
| [$Ser^3$,$Ala^4$]Vc1.1(1-8) or [S4A]Vc1.1(1-8) | SEQ ID No. 5 | G C S A D P R C | 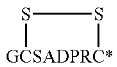 |
| [$Ser^3$,$Ala^5$]Vc1.1(1-8) or [D5A] Vc1.1 | SEQ ID No. 11 | G C S S A P R C | 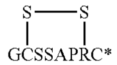 |
| [$Ser^3$,$Ala^7$]Vc1.1(1-8) or [R7A] Vc1.1 | SEQ ID No. 12 | G C S S D P A C | 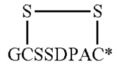 |
| [$Glu^2$,$Ser^3$,$Lys^8$]Vc1.1(1-8) or Vc1.1(1-8)amide 8-membered | SEQ ID No. 24 | G E S S D P R K | 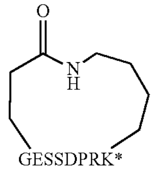 |
| [$Asp^2$,$Ser^3$,$Lys^8$]Vc1.1(1-8) or Vc1.1(1-8)amide 7-membered | SEQ ID No. 25 | G D S S D P R K | 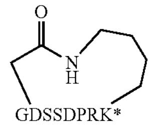 |
| [$Asp^2$,$Ser^3$,$Orn^8$]Vc1.1(1-8) or Vc1.1(1-8)amide 6-membered | SEQ ID No. 26 | G D S S D P R X | 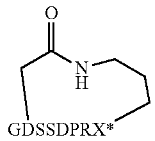 |
| Vc1.1(1-8)DCA | SEQ ID NO. 4 | G C S S D P R C | 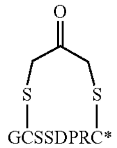 |
| Vc1.1(1-8) thioether (1) | SEQ ID No. 27 | G C S S D P R A | 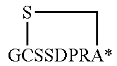 |

-continued

| Designated name | SEQ ID NO. | Sequence | Structure |
|---|---|---|---|
| Vc1.1(1-8) thioether (2) | SEQ ID No. 28 | G A S S D P R C | 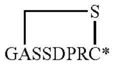 |
| [$Ser^4$]Pu1.2 (1-9) or [C4S]Pu1.2 | SEQ ID No. 29 | G G C S S Y P P C | 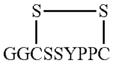 |
| [$Ser^3$]Vc1.1(2-8) or Vc1.1(2-8) | SEQ ID No. 19 | C S S D P R C | 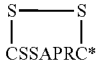 |
| c(Vc1.1(2-8))$_2$ | SEQ ID No. 37 | C S S D P R C S S D P R | 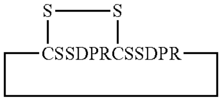 |
| SFTI-1(Vc1.1(1-8))A | SEQ ID No. 38 | G C S S D P R C T K S I P P | 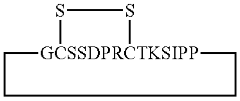 |
| SFTI-1(Vc1.1(1-8))B | SEQ ID No. 39 | G G C S S D P R C F P D | 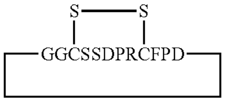 |
| [$Ser^3$, $Ala^9$]Vc1.1(1-9) | SEQ ID No. 30 | G C S S D P R C A* | 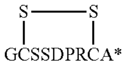 |
| [$Ser^3$, $Trp^9$]Vc1.1(1-9) | SEQ ID No. 31 | G C S S D P R C W* | 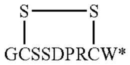 |
| [$Ser^3$, $Arg^9$]Vc1.1(1-9) | SEQ ID No. 32 | G C S S D P R C R* | 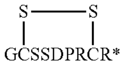 |
| [$Ser^3$, $Lys^9$]Vc1.1(1-9) | SEQ ID No. 33 | G C S S D P R C K* | 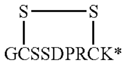 |
| [$Ser^3$, $Asp^9$]Vc1.1(1-9) | SEQ ID No. 34 | G C S S D P R C D* | 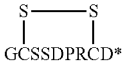 |
| [$Ser^3$,$Lys^4$]Vc1.1(1-8) | SEQ ID No. 6 | G C S K D P R C* | 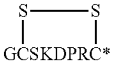 |
| [$Ser^3$,$Asn^4$]Vc1.1(1-8) or [S4N]Vc1.1(1-8) | SEQ ID No. 7 | G C S N D P R C* | 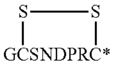 |
| [$Ser^3$,$Thr^4$]Vc1.1(1-8) or [S4T]Vc1.1(1-8) | SEQ ID No. 8 | G C S T D P R C* | 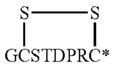 |
| [$Ser^3$,His4]Vc1.1(1-8) or [S4H]Vc1.1(1-8) | SEQ ID No. 9 | G C S H D P R C* | 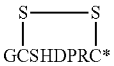 |
| [$Ser^3$,Arg4]Vc1.1(1-8) or [S4R]Vc1.1(1-8) | SEQ ID No. 10 | G C S R D P R C* | 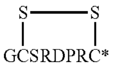 |
| [$Asp^3$]Vc1.1(1-8) or [S3D]Vc1.1(1-8) | SEQ ID No. 21 | G C D S D P R C* | 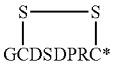 |
| [$Val^3$]Vc1.1(1-8) or [S3V]Vc1.1(1-8) | SEQ ID No. 22 | G C V S D P R C* | 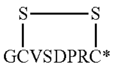 |

-continued

| Designated name | SEQ ID NO. | Sequence | Structure |
|---|---|---|---|
| RgIA(1-10) | SEQ ID No. 35 | G C S S D P R C R Y* | 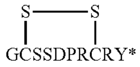 |
| [Ser3]Vc1.1(1-12) | SEQ ID No. 36 | G C S S D P R C N Y D H* | 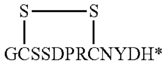 |
| [Ser3]Vc1.2(1-8) or [C3S]Vc1.2(1-8) | SEQ ID No. 13 | G C S S N P A C* | 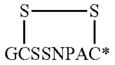 |
| [Ser3]RgIA(1-8) or [C3S]RGIA(1-8) | SEQ ID No. 14 | G C S S D P R C* | 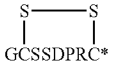 |
| [Ser3]PeIA(1-8) or [C3S]PeIA(1-8) | SEQ ID No. 15 | G C S S H P A C* | 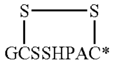 |
| [Ser3]AuIB(1-8) or [C3S]AuIB(1-8) | SEQ ID No. 16 | G C S S Y P P C* | 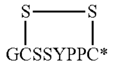 |

Note:
*indicates an amidated C-terminus.

The peptides according to the present invention may be in the form of salts. The salts of the compounds of the invention are preferably pharmaceutically acceptable, but it will be appreciated that non-pharmaceutically acceptable salts also fall within the scope of the present invention, since these are useful as intermediates in the preparation of pharmaceutically acceptable salts or may be useful in some applications, such as probes or assays.

The pharmaceutically acceptable salts include acid addition salts, base addition salts, salts of pharmaceutically acceptable esters and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicyclic, sulfamic, or tartartic acids. The counter ion of quarternary amines and pyridiniums include chloride, bromide, iodide, sulfate, phosphate, methansulfonate, citrate, acetate, malonate, fumarate, sulfamate, and tartate. The base addition salts include but are not limited to salts such as sodium, potassium, calcium, lithium, magnesium, ammonium and alkylammonium. The salts may be made in a known manner, for example by treating the compound with an appropriate acid or base in the presence of a suitable solvent.

The peptides useful according to the invention may be in crystalline form and/or in the form of solvates (e.g. hydrates) and it is intended that all of these forms be within the scope of the present invention. The term "solvate" is a complex of variable stoichiometry formed by a solute (in this invention, a compound of the invention) and a solvent. Such solvents should not interfere with the biological activity of the solute. Methods of solvation are generally known within the art.

The compounds of the present invention may be used as pharmaceuticals. Accordingly, in another aspect the present invention provides a composition comprising a peptide according to the present invention, and a pharmaceutically acceptable carrier or diluent.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives, care should be taken to ensure that the activity of the peptide is not destroyed in the process and that the peptide is able to reach its site of action without being destroyed. In some circumstances it may be necessary to protect the peptide by means known in the art, such as, for example, micro encapsulation. Similarly the route of administration chosen should be such that the peptide reaches its site of action.

In some embodiments, a peptide or a composition comprising a peptide of the invention may be administered orally, intravenously, subcutaneously, intraperitoneally, or rectally.

The pharmaceutical forms suitable for injectable use include sterile injectable solutions or dispersions, and sterile powders for the extemporaneous preparation of sterile injectable solutions. They should be stable under the conditions of manufacture and storage and may be preserved against reduction or oxidation and the contaminating action of microorganisms such as bacteria or fungi.

Those skilled in the art may readily determine appropriate formulations for the peptides of the present invention using conventional approaches. Identification of preferred pH ranges and suitable excipients, for example antioxidants, is routine in the art (see for example Cleland et al, 1993). Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intraperitoneal, subcutaneous, intracerebral, intrathecal and epidural injection or infusion. In one embodiment, the composition is for intraperitoneal, subcutaneous or intravenous administration, especially intraperitoneal or subcutaneous administration.

Sterile injectable solutions are prepared by incorporating the active compounds in the required amount in the appropriate solvent with various other ingredients such as those enumerated above, as required, followed by filtered sterilization. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

Other pharmaceutical forms include oral and enteral formulations of the present invention, in which the active peptide may be formulated with an inert diluent or with an assimilable edible carrier, or it may be enclosed in a hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. It will be appreciated that some of these oral formulation types, such as buccal and sublingual tablets, have the potential to avoid liver metabolism. However the peptides of the present invention may also be delivered to the stomach where liver metabolism is likely to be involved. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the active peptide to specific regions of the gut.

Liquid formulations may also be administered enterally via a stomach or oesophageal tube.

Enteral formulations may be prepared in the form of suppositories by mixing with appropriate bases, such as emulsifying bases or water-soluble bases. It is also possible, but not necessary, for the peptides of the present invention to be administered topically, intranasally, intravaginally, intraocularly and the like.

The present invention also extends to any other forms suitable for administration, for example topical application such as creams, lotions and gels, or compositions suitable for inhalation or intranasal delivery, for example solutions, dry powders, suspensions or emulsions. The present invention also extends to parenteral dosage forms, including those suitable for intravenous, subcutaneous, intramuscular, intrathecal, and intracerebral or epidural delivery.

The conotoxins useful according to the present invention may be administered by inhalation in the form of an aerosol spray from a pressurised dispenser or container, which contains a propellant such as carbon dioxide gas, dichlorodifluoromethane, nitrogen, propane or other suitable gas or combination of gases. The compounds may also be administered using a nebuliser.

Pharmaceutically acceptable vehicles and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable vehicle. The specification for the novel dosage unit forms of the invention are dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired as herein disclosed in detail.

As mentioned above the principal active ingredient is compounded for convenient and effective administration in effective amounts with a suitable pharmaceutically acceptable vehicle in dosage unit form. A unit dosage form can, for example, contain the principal active compound in amounts ranging from 0.25 μg to about 2000 mg. Expressed in proportions, the active compound is generally present in from about 0.25 μg to about 2000 mg/ml of carrier. In the case of compositions containing supplementary active ingredients, the dosages are determined by reference to the usual dose and manner of administration of the said ingredients.

In another aspect of the present invention there is provided a method of treating or preventing a disease or condition in respect of which modulation of the activity of an N-type or R-type calcium channel is associated with effective treatment, comprising administering to a subject in need thereof an effective amount of a peptide of the present invention.

Preferably the subject is in need of such treatment, although the peptide may be administered in a prophylactic sense.

In a further aspect, the present invention provides a use of a peptide of the present invention in the manufacture of a medicament for the treatment of a condition or disease in respect of which inhibition of an N-type or R-type calcium channel is associated with effective treatment.

The diseases or conditions with which modulation of the activity of an N-type or R-type calcium channel are associated include a wide range of conditions and diseases, such as the reduction of neuronal damage following ischemia, production of analgesia, enhancement of opiate analgesia, treatment of schizophrenia, stimulant induced psychoses, alcoholism, convulsions, hypertension, inflammation and diseases which cause bronchoconstriction, and in the inhibition of progression of chronic and neuropathic pain. It has also been found that N-type and R-type VGCCs are involved in conditions including hyperalgesia and allodynia associated with neuropathic and inflammatory pain. Furthermore, blockage of N-type or R-type VGCCs may be useful in the treatment of acute, chronic, inflammatory and neuropathic pain, visceral pain and breakthrough pain.

The alpha7 nAChR ($\alpha$7 nAChR) subtype has been implicated in a range of neurological diseases including schizophrenia, bipolar disorder, Alzheimer's and Parkinson's diseases, drug dependence, inflammation. Compounds which target $\alpha$7 nAChR may be useful as therapeutics for the treatment of one or more of these conditions.

Other conditions that have been associated with inhibition of an N-type and R-type calcium channel include overactive bladder, modulation of a drug related effect or behaviour, non-inflammatory gastrointestinal disorders and prevention or treatment of retinal or optic nerve head damage resulting from acute traumatic or acute ischemic events. Gastrointestinal disorders may include, for example, hiatal hernias, strictures, esophageal webs, Schatzki's ring, esophageal diverticula, esophageal scleroderma, motor disorders of the esophagus, such as achalasia and diffuse esophageal spasm, and irritable bowel syndrome. Drug related effects or behaviours include, for example, effects from ethanol, cannabinoids and opioids, such as stimulant, sedative, hypnotic and ataxic effects and also drug reward.

In another aspect of the present invention there is provided a method for reducing neuronal damage following ischemia, for the production of analgesia, for enhancement of opiate analgesia, for modulation of a drug related effect or behaviour, or for the treatment of pain, schizophrenia, stimulant induced psychoses, hypertension, inflammation, overactive bladder, non-inflammatory gastrointestinal disorders, or diseases which cause bronchoconstriction, comprising administering to a subject in need thereof an effective amount of a peptide of the present invention.

The present invention also provides the use of a peptide of the present invention in the manufacture of a medicament for reducing neuronal damage following ischemia, for the production of analgesia, for enhancement of opiate analgesia, for modulation of a drug related effect or behaviour, or for the treatment of pain, schizophrenia, stimulant induced psychoses, hypertension, inflammation, overactive bladder, non-inflammatory gastrointestinal disorders, or diseases which cause bronchoconstriction.

In another aspect of the present invention there is provided a method for treating neuronal damage following ischemia, production of analgesia, enhancement of opiate analgesia, treatment of schizophrenia, stimulant induced psychoses, alcoholism, convulsions, hypertension, inflammation and diseases which cause bronchoconstriction, and in the inhibition of progression of acute, chronic, inflammatory and neuropathic pain, visceral pain and breakthrough pain, bipolar disorder, Alzheimer's and Parkinson's diseases, or drug dependence comprising administering to a subject in need thereof an effective amount of a peptide of the present invention.

In another aspect of the present invention there is provided a method of treating or preventing chronic, visceral or neuropathic pain comprising administering to a subject in need thereof an effective amount of a peptide according to the present invention. In a further aspect, the present invention provides a method for the treatment of neuropathic pain, inflammatory pain or breakthrough pain, comprising administering to a subject in need thereof an effective amount of a peptide according to the present invention.

In another aspect, the present invention provides a use of a peptide according to the present invention in the manufacture of a medicament for the treatment of chronic, visceral or neuropathic pain. In a further aspect there is provided a use of a peptide according to the present invention in the manufacture of a medicament for the treatment of neuropathic pain, inflammatory pain or breakthrough pain.

While the peptide according to the invention may be the sole active ingredient administered to the subject, the administration of other active ingredients with said peptide is within the scope of the invention. For example, the peptide could be administered with one or more therapeutic agents, including other VGCC agonists or antagonists.

In another aspect of the present invention there is provided a method for enhancing analgesia, comprising administering to a subject in need thereof an effective amount of a peptide according to the present invention in combination with an effective amount of compound that has analgesic activity. In a further aspect there is provided a use of a peptide according to the present invention in the manufacture of a medicament for enhancing analgesia, wherein the peptide is for administration with a compound that has analgesic activity.

Suitable compounds that have analgesic activity include morphine, gabapentin, a monoamine transporter inhibitor, Cymbalta® (duloxetine hydrochloride) or a non-steroidal anti-inflammatory drug (NSAID).

The peptides of the present invention may be administered by any appropriate route including oral, intravenous, intracerebroventricular, intramuscular, intraperitoneal, subcutaneous, intracerebral, intrathecal and epidural administration, especially intravenous, intraperitoneal and subcutaneous administration.

In one embodiment, the peptides of the present invention are used in the treatment of pain. This includes inflammatory pain, neuropathic pain, chronic pain, visceral pain and breakthrough pain. The peptides may be administered to target the central nervous system (for example by oral, intrathecal, intracerebroventricular or intracerebral administration) or the peripheral nervous system (for example by subcutaneous, intraperitoneal or intravenous administration).

In a further aspect, the present invention provides a method of modulating the activity of an N-type or R-type calcium channel, comprising contacting the N- or R-type calcium channel with a peptide according to the present invention. This method may be conducted in vitro or in vivo. In a preferred embodiment, the method is conducted in vitro. This method includes, but is not limited to, screening of compound libraries to identify compounds that bind to an N- or R-type calcium channel, assays to determine the biological activity of compounds that bind to an N- or R-type calcium channel, or experiments to investigate the physiology or pharmacology of an N- or R-type calcium channel. This method may also result in the treatment or prophylaxis of conditions or diseases in animals, such as humans.

As used herein, modulation of N- or R-type calcium channels includes selective inhibition of the N- or R-type calcium channel, selective inhibition of subunits of the N- or R-type calcium channel.

As used herein, the term "N-type VGCC" or "N-type calcium channel" includes any subtype or subunit of the N-type VGCC. The term also relates to N-type VGCCs found naturally in microorganisms and animals, including in humans, and also recombinant and synthetic receptors.

As used herein, the term "R-type VGCC" or "R-type calcium channel" includes any subtype or subunit of the R-type VGCC. The term also relates to R-type VGCCs found naturally in microorganisms and animals, including in humans, and also recombinant and synthetic receptors.

Peptides according to the present invention have been shown to have selectivity for N- or R-type VGCCs over P/Q-type VGCCs. At the concentrations tested, peptides of the present invention have been shown to have no effect at other types of VGCCs, including L-, and T-type VGCCs. The terms "selective" and "selectivity" as used herein mean that the binding activity for a given concentration of the peptide at the N- or R-type VGCC is typically greater than the binding activity at, for example, the P/Q-type VGCC. Those skilled in the art would be able to readily determine the selectivity of the peptides for these VGCCs using standard techniques.

Peptides of the present invention have also been shown to exhibit different binding and reversibility characteristics when different subunits are present in the N- or R-type VGCC. This may result in peptides of the present invention having differing activities in different tissues and/or in conditions or disease states, potentially allowing greater selectivity in treatment. This is because variants of the N- or R-type VGCC have been shown to exhibit different expression levels in various tissues and it has also been shown that subunits of the N- or R-type VGCC may be upregulated in different conditions or disease states. For example, N-type calcium channels which comprise a $\beta_{2a}$ subunit are believed to be located supraspinally. Moreover, it has also been shown that a feature of neuropathic pain is the upregulation of the $\alpha_2\delta_1$ subunit that associates with VGCC in dorsal root ganglia.

The terms "reversible" and "reversibly" as used herein mean that following inhibition of the N- or R-type VGCC, the N- or R-type VGCC substantially returns to its state prior to inhibition. Those skilled in the art would readily be able to determine the reversibility of the peptides of the invention at the VGCCs using standard techniques.

The present invention also extends to the use of the peptides of the invention in assays and screens to identify compounds with desired activity. In such assays and screens, the peptides of the present invention may be unlabeled or may include a radioactive or fluorescent label.

In one aspect, the present invention provides a method of assaying a compound for its ability to modulate the activity of voltage gated calcium channel, comprising the steps of: a) contacting the N-type or R-type calcium channel with a peptide according to the present invention in the presence of the compound; and b) detecting an interaction between the peptide to the N-type or R-type calcium channel, wherein displacement of the binding is indicative of a compound that modulates the activity of the N-type or R-type calcium channel.

The term "contacting" refers to mixing or combining said conotoxin peptide, said compound and said voltage gated calcium channel in a solution. This may be at room temperature, or at lower or higher temperatures than room temperature. In one embodiment, the solution may be a buffered solution designed to promote binding. The solution may or may not be agitated. The solution may also be applied in a static manner or a continuous perfusion.

As used herein, a compound is taken to modulate the activity of an N-type or R-type calcium channel when an interaction between the compound and the channel can be determined by a person skilled in the art. In this context, "interact" or variants thereof, such as "interacting" or "interaction, is used in the broadest sense, including interaction at calcium channel binding site, allosteric interaction, and also interaction at one or more subunits of the N- or R-type calcium channel. Preferably, this interaction would be sufficient to inhibit the receptor.

Accordingly, in another aspect the present invention provides a method of testing the N-type or R-type calcium channel binding activity of a test peptide or compound, comprising (1) determining the level of binding of a peptide according to the present invention to N-type calcium channels in the absence of said test peptide or compound, (2) determining the level of binding of said peptide of the invention to N-type or R-type calcium channels in the presence of said test peptide or compound, and (3) comparing the level determined in step (1) to the level determined in step (2).

In a further aspect, the present invention provides a method of screening for identifying compounds which bind to N-type or R-type calcium channels, comprising (1) determining the level of binding of a peptide according to the present invention to N-type or R-type calcium channels in the absence of a test compound, (2) determining the level of binding of said peptide of the invention to N-type or R-type calcium channels in the presence of said test compound, and (3) comparing the level determined in step (1) to the level determined in step (2), thereby identifying compounds which bind to N-type or R-type calcium channels.

Through these methods, compounds that modulate the activity of N-type or R-type calcium channels may be identified, and/or the activity of these compounds determined. The compounds to be tested could be produced synthetically, or through biological processes. Mixtures of compounds may also be tested, which may, for example, include testing of crude cone snail venom or extracts thereof. These compounds may be used as, or used to develop, new pharmaceuticals that target N-type calcium channels. For example, new pharmaceuticals may be developed through identifying new lead compounds or through studying the binding interaction between the peptides of the present invention and N-type or R-type calcium channels.

The peptides of the present invention may be used, possibly in a labelled form such as radiolabelled form, to run assays and/or screens to identify compounds which interact with N-type or R-type calcium channels and/or particular subunits of such channels. Those skilled in the art could readily establish such assays and/or screens.

Accordingly, a further embodiment the present invention provides a peptide of the present invention wherein at least one of the amino acids incorporates a radiolabel. Radiolabels may include, for example, $^{125}I$, $^{131}I$, $^{14}C$, $^{15}N$, $^{35}S$ or $^{3}H$. If $^{125}I$ is used, for example, the iodine could be attached to tyrosine or another appropriate reside. If no such residue exists, an amino acid incorporation/substitution scan could be conducted to establish a suitable location to incorporate/substitute such a residue. In other examples, within the peptide one or more hydrogens may be replaced with $^{125}I$, $^{131}I$ or $^{3}H$; one or more carbons may be replaced with $^{14}C$; or one or more nitrogens may be replaced with $^{15}N$. A variety of labelled versions of the compounds of the present invention may be readily prepared by standard methods and assessed for retention of their ability to bind to N-type or R-type VGCCs in standard assays. Labelled versions of the compounds which do retain the ability to modulate the activity of N-type or R-type VGCCs or binding portions of such channels could then be used in assays and/or screens.

Radioligand binding assays may be performed using N-type or R-type calcium channels and the labelled conotoxin peptide. The calcium channel may be incubated with the labelled peptide and the compound to be tested for activity at the N-type or R-type calcium channel. In one embodiment, these components are prepared for use as separate solutions of known concentrations. After binding is complete, the calcium channel is separated from the labelled peptide and the compound, such as through filtration. The amount of binding that has occurred is then determined and/or binding is then detected.

Non-specific binding may be determined by incubating the calcium channel with an excess of the unlabeled conotoxin peptide in the presence of the labelled peptide. For example, if labelled conotoxin was used in the assay, then unlabeled conotoxin would be used to determine non-specific binding. After incubation, the assay is conducted in the same manner as above. Non specific binding should be subtracted from total binding when calculating the specific binding for each compound tested. If necessary, other steps such as washing, filtering, shaking and stirring may be included in the assay procedure as necessary. Normally, wash steps are included following separation of the membrane-bound compound from the compound remaining in solution to enable quantification of the amount of compound that has bound (e.g. such as by counting a radioactive isotope). Specific binding is compared with the binding obtained when the calcium channel is incubated in the presence of the labelled peptide alone to determine the extent to which the test compound has displaced the labelled peptide.

Care should be taken to avoid artefacts when performing these assays. Such artefacts could make it appear that the compound to be tested binds to the calcium channel when it does not, or vice versa. For example, a buffer solution should be chosen for the assay that does not affect the binding of the compounds to the calcium channel. Similarly, preparations of test compounds should not have proteolytic activity. It is also desirable that the compounds that are identified to bind to the calcium channel are examined in a sufficient concentration range to enable a Scatchard analysis on the results. This type of analysis is well known in the art and can be assisted using computer programs.

Fluorescent labels may also be incorporated into peptides of the present invention. Fluorescent labelling compounds may include: cyanine 3 (Cy3), cyanine 5 (Cy5), 4,4-difluoro-4-bora-3a,4α-diaza-s-indacene (BODIPY), nitrobenzoxadiazole (NBD), 4-nitro-O-phenylenediamine (NPD), fluorescein, fluorescein isothiocyanate, rhodamine, methylrhodamine, tetramethylrhodamine, phycoerythrin, phycocyanin, allophycocyanin, o-phthaldehyde and fluorescamine. Fluorescent streptavidin may also be used in conjunction with biotin. Such fluorescent labels may be incorporated at the N- or C-terminus of the peptides of the present invention, or may be incorporated in selected loops of these peptides. For example, the labels may be attached through an existing chemically reactive amino acid, at a position that does not have a substantial adverse effect on binding between the peptide and the VGCC.

Therefore, according to a further embodiment of the peptides of the present invention, at least one of the amino acids in the peptide incorporates a radiolabel or a fluorescent label.

The methods may also include electrophysiological studies, such as patch clamp, intracellular recording and extracellular recording studies (Purves 1991; Brock and Cunnane 1987; Smith and Cunnane 1997; Hamill et al., 1981). In such studies membrane potential, whole cell and single channel currents may be measured, providing information on neurotransmitter release from nerve terminals and changes in ionic currents and membrane potential. The studies can be carried out on the following cells which include, but are not limited to, *Xenopus* oocytes, cultured neurones such as sensory neurones (eg. dorsal root ganglia), parasympathetic neurones (eg. submandibular and intracardiac ganglia), sympathetic neurones (eg. pelvic ganglia) and central neurones. The studies can also be carried out on whole nerve preparations such as CNS or peripheral ganglion preparations, or peripheral neuro-effector tissues, including, but not limited to, guinea pig vas deferens, rat anococcygeus, guinea pig ileum, rat bladder, mammalian colon, mammalian artery, mammalian atria and rat trachea. For example, a candidate compound-evoked change in calcium current in a cell may be measured compared to a control when the cell is electrically stimulated.

The VGCC may be activated using a technique suitable for the assay or screen being performed. For cell based assays this may be achieved by depolarising the membrane, such as by applying a high concentration of potassium ions or by applying a current across the membrane. A cell can be depolarised by changing extracellular potassium concentration in the physiological salt solution that is bathing the cell. For example normal potassium concentration in a physiological salt solution is 4.0 to 5.0 mM (preferably, around 4.5-4.7 mM). Increasing the potassium concentration above 5 mM will start to depolarise the cell. Increasing the concentration above 20 mM to 150 mM will most certainly depolarise the cell, with maximum depolarisation being evoked by 150 mM. For organ based assays field stimulation would be required to activate the voltage-dependent calcium channels (Smith and Cunnane 1997; Smith and Cunnane 1996).

When measuring candidate compound-evoked changes in calcium channel current, the channel must be stimulated in order to observe an effect. The frequency of stimulation is important to observe the inhibition of the calcium channel current. For example pulses of 2 to 20 Hz at 2 to 10 second intervals for approximately 1 to 20 minutes can be used. Such frequencies would be used in tissue bath studies and intracellular and extracellular recording from smooth muscle cells or postganglionic nerves or preparations such as brain slices. If the duration of the stimulus (depolarising pulse) is too brief and infrequent then no inhibition is observed. On the other hand, if either the duration of the stimulus (depolarising pulse) or frequency is increased then the effect of inhibiting the calcium channel current is enhanced.

The rate of block of the calcium channel current in the presence of a test peptide or compound may be increased with higher frequencies of stimulation (depolarising pulses) such as may occur in intense pain. In conducting such assays and screens the frequency of activation of the calcium channels should preferably be greater than or equal to 0.1 Hz. The method of activation of VGCCs is by applying a depolarising voltage step from −80 mV to 0 mV. Both the duration of the voltage step (or pulse) and frequency of applying the voltage step influence the rate of inhibition (block) of the calcium current in the presence of the test peptide or compound, whereby increasing either the duration or frequency increase the rate of block analogous to the use-dependent block by local anaesthetics of voltage-dependent sodium channels (see Hile et al. 1975).

In another embodiment, the methods may include tissue or organ bath studies. Nerve-evoked contraction or relaxation of muscle may be measured in the presence and absence of conotoxin peptides to investigate whether the conotoxin can inhibit tissue contraction or relaxation (Neumann et al. 1999; Bettler et al. 2004; Bowery et al. 2002). Suitable tissues for such studies include: ileum, arteries, bladder, anococcygeus, atria, ventricular muscle, vas deferens, diaphragm, trachea and colon.

The methods may also include other assays as described in the Examples.

In some of the methods discussed above, it may be necessary to produce a recombinant calcium channel. To produce a recombinant calcium channel, the DNA sequence for the calcium channel may be obtained and then incorporated into an expression vector with an appropriate promoter. Once the expression vector is constructed, it may then be introduced into the appropriate cell line using methods including $CaCl_2$, $CaPO_4$, microinjection, electroporation, liposomal transfer, viral transfer or particle mediated gene transfer.

The host cell may comprise prokaryote, yeast or higher eukaryote cells. Suitable prokaryotes may include, but are not limited to, eubacteria, such as Gram-negative or Gram-positive organisms, including Enterobacteriaceae. Such Enterobacteriaceae may include Bacilli (e.g. *B. subtilis* and *B. licheniformis*), *Escherichia* (e.g. *E. coli*), *Enterobacter, Erwinia, Klebsiella, Proteus, Pseudomonas* (e.g. *P. aeruginosa*), *Salmonella* (e.g. *Salmonella typhimurium*), *Serratia* (e.g. *Serratia marcescens*), *Shigella*, and *Streptomyces*. Suitable eukaryotic microbes include, but are not limited to, *Candida, Kluyveromyces* (e.g. *K. lactis, K. fragilis, K. bulgaricus, K. wickeramii, K. waltii, K. drosophilarum, K. thermotolerans* and *K. marxianus*), *Neurospora crassa, Pichia pastoris, Trichoderna reesia, Saccharomyces cerevisiae, Schizosaccharomyces pombe, Schwanniomyces* (e.g. *Schwanniomyces occidentalis*), and filamentous fungi (e.g. *Neurospora, Penicillium, Tolypocladium*, and *Aspergillus* (e.g. *A. nidulans* and *A. niger*)) and methylotrophic yeasts (e.g. *Hansenula, Candida, Kloeckera, Pichia, Saccharomyces, Torulopsis*, and *Rhodotorula*). Suitable multicellular organisms include, but are not limited to, invertebrate cells (e.g. insect cells including *Drosophila* and *Spodoptera*), plant cells, and mammalian cell lines (e.g. Chinese hamster ovary (CHO cells), monkey kidney line, human embryonic kidney line, mouse sertoli cells, human lung cells, human liver cells and mouse mammary tumor cells). An appropriate host cell can be selected without undue experimentation by a person skilled in the art.

The cell line may then be cultured in conventional nutrient media modified for inducing promoters, selecting transformants, or amplifying the genes encoding the desired sequences. Culture conditions, such as media, temperature, pH, and the like, can be selected without undue experimentation by the person skilled in the art (for general principles, protocols and practical techniques, see Butler, M. 1991; Sambrook 1989). The cells may then be selected and assayed for the expression of the calcium channel using standard procedures.

Unless stated otherwise, any assays on these receptors may be performed in vivo or in vitro. If calcium channels for said assays are produced through cellular processes, either intact cells or membranes prepared for the cells may be used.

The peptides according to the present invention may be prepared using standard peptide synthetic methods followed by oxidative disulfide bond formation, for example as discussed in the Examples. For example, the linear peptides may be synthesised by solid phase methodology using BOC chemistry, as described by Schnolzer et al., 1992. Following deprotection and cleavage from the solid support the reduced peptides are purified using preparative chromatography. The purified reduced peptides are oxidised in buffered systems. The oxidised peptides are purified using preparative chromatography. Reduction/alkylation techniques can be used to determine the disulfide bond connectivities using well documented procedures (Shon et al. 1997; Bures et al. 1998). The peptides can also be made using selective oxidative disulfide bond formation using the procedures outlined in Kent et al. 1998.

General references describing the synthesis of conotoxins include Sato et al. 1991; Lew et al. 1997; Flinn et al. 1995 and WO 91/07980.

If an unsubstituted amide is desired at the C-terminus of the peptide, BHA or MBHA resin is preferred, as these resins provide the unsubtituted amide directly on cleavage. If N-methylamide is desired at the C-terminus of the peptide, then N-methyl BHA resin may be used. Should other N-substituted amides be desired, then techniques such as those disclosed in U.S. Pat. No. 4,569,967 may be followed, or alternatively it may be preferable to functionalise the C-terminus via solution phase methods.

Alternatively, it may be desired to link the C-terminus of the conotoxin peptide to the N-terminus by a linker. There are several ways in which linear conotoxins may be cyclised, for example as outlined in Australian Patent Application No. 2006236006.

In a first approach, an extended linear peptide is first synthesised "on resin" using solid phase peptide synthesis methods. This extended linear peptide comprises the native sequence starting at a cysteine residue at, or closest to, the N-terminus and a C-terminal extension comprises the new linking moiety. Solid phase peptide synthesis may be synthesised using BOC chemistry, as described by Schnolzer et al., 1992. In another embodiment, Fmoc chemistry may be used. Following deprotection and cleavage, the extended conotoxin peptide is cyclised to a thioester intermediate which subsequently rearranges to an amine-cyclised peptide. This reduced peptide is then oxidised to form the disulfide bonds.

In another approach, the peptide is assembled using solid phase peptide synthesis methods as before. The additional residues may be added at the N- and/or C-termini, and following synthesis the peptide is deprotected and cleaved from resin. Preferably in this embodiment the N- and C-termini of the synthesised peptide are glycine residues. The peptide is then folded. Following cyclisation the N- and C-termini are coupled together. However, this approach may be complicated if large numbers of lysine, glutamic acid or aspartic acid residues are present in the sequence.

A third approach is to begin with an oxidised, mature conotoxin. A peptide linker may then be synthesised and ligated with the conotoxin using published procedures for the ligation of peptides. The extended peptide is then cyclised.

Other approaches are also possible, provided that the product is a cyclised conotoxin peptide having the required disulfide bonds. For example, the peptide may be synthesised using solution phase methods, or selective deprotection of cysteine residues may be employed.

The peptides of the present invention may also be prepared using recombinant DNA technology. A nucleotide sequence encoding the desired peptide sequence may be inserted into a suitable vector and protein expressed in an appropriate expression system, as previously discussed for recombinant calcium channels. In some instances, further chemical modification of the expressed peptide may be appropriate, for example C-terminal amidation. Under some circumstances it may be desirable to undertake oxidative bond formation of the expressed peptide as a chemical step following peptide expression. This may be preceded by a reductive step to provide the unfolded peptide. Those skilled in the art may readily determine appropriate conditions for the reduction and oxidation of the peptide.

In a further aspect the present invention provides an isolated nucleic acid molecule comprising a sequence of nucleotides encoding or complementary to a sequence encoding a peptide according to the present invention.

The nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules of the present invention are generally in isolate form, they may be integrated into or ligated to or otherwise fused or associated with other genetic molecules such as vector molecules and in particular expression vector molecules, such as those discussed above.

In a further aspect, the present invention contemplates a genetic construct comprising a nucleic acid capable of encoding a peptide according to the present invention. Preferably, the nucleic acid portion is operably linked to a promoter, such that the promoter is capable of directing expression of the nucleic acid in an appropriate cell.

In another aspect the present invention provides a nucleic acid probe comprising a sequence of nucleotides encoding or complementary to a sequence encoding all or part of a peptide according to the present invention.

As used herein a reference to a "probe" includes reference to a primer used in amplification or a probe for use in direct hybridization.

Still another aspect of the present invention relates to a monoclonal or polyclonal antibody to a peptide according to the present invention. Such antibodies may be selected from naturally occurring antibodies to the peptides of the present invention or may be specifically raised to the peptides using standard techniques. In the case of the latter, the peptides may first need to be associated with a carrier molecule. The antibodies of the present invention may be particularly useful as therapeutic or diagnostic agents.

In this regard, specific antibodies can be used to screen for the peptides according to the invention. Techniques for such assays are well known in the art and include, for example, sandwich assays and ELISA. Knowledge of peptide levels may be important for monitoring certain therapeutic protocols.

Certain embodiments of the invention will now be described with reference to the following examples which are intended for the purpose of illustration only and are not intended to limit the scope of the generality hereinbefore described.

EXAMPLES 2-(1H-Benzotriazol-1-yl)-1,1,3,3-tetramethyluronium hexafluorophosphate (HBTU) and 9H-fluoren-9-ylmethoxycarbonyl (Fmoc) protected L-amino acids were obtained from Iris Biotech (Germany). N,N-Dimethylformamide (DMF) and HPLC-grade acetonitrile were from VWR. Peptide synthesis-grade trifluoroacetic acid (TFA) and diethyl ether were purchased from Halocarbon, USA. GABA and R-(+)-baclofen hydrochloride were purchased from Sigma-Aldrich Pty. Ltd. (Sydney, Australia), CGP55845 hydrochloride was purchased from Tocris Bioscience (Bristol, UK), and ω-conotoxin CVIE was a gift from Prof. Paul F. Alewood (The University of Queensland, Australia). Peptide concentrations were determined using a Direct Detect® IR spectrometer (Merck Millipore).

Animal studies were conducted in accordance with the guidelines set out in the Australian Code of Practice for the Care and Use of Animals for Scientific Purposes, 8th edition, 2013 and animal ethics approval has been obtained from the University of Queensland Animal Ethics Committee.

Data are mean±SEM (n, number of experiments). Statistical analyses were performed using the Student's t-test for two groups, and one-way ANOVA or two-way ANOVA for multiple comparisons; differences were considered significant if $p<0.05$.

Example 1: General Procedure for Peptide Synthesis

Unless otherwise note, peptides were assembled on rink amide methylbenhydrylamine (MBHA) resin by manual solid phase peptide synthesis (SPPS)[2] or using a Symphony synthesizer (Protein Technologies, Inc). All peptides were synthesized with Fmoc chemistry using an in situ neutralization/HBTU protocol.

For peptides used in the random oxidation trials, Cys(trt) was incorporated at all four positions. Peptides were cleaved from resin using trifluoroacetic acid (TFA) with triisopropylsilane (TIPS) and water as scavengers (9:0.5:0.5 TFA:TIPS:water) at room temperature (21-23° C.) for 2 h. TFA was removed under vacuum, and the peptide was precipitated in ice-cold ether, filtered and dissolved in 50% acetonitrile containing 0.05% TFA, then lyophilized. Crude peptides were purified by reverse phase-HPLC (RP-HPLC) on a C18 column using a gradient of 0-80% B (Buffer A: $H_2O$/0.05% TFA; Buffer B: 90% $CH_3CN$/10% $H_2O$/0.045% TFA) in 80 min. Electrospray-mass spectroscopy (ES-MS) confirmed the molecular mass of the synthesized peptide, which was lyophilized before a two-step oxidation protocol was used.

The truncated peptides, such as [$Ser^4$]Pu1.2(1-9) and [$Ser^3$]Vc1.1(1-8), were synthesized on rink amide MBHA resin using Fmoc chemistry as described above. Peptides were cleaved from the resin using TFA with TIPS and water as scavengers (9:0.5:0.5 TFA:TIPS:water) at room temperature for 2 h. Crude peptides were purified by RP-HPLC.

Where appropriate, a selective disulfide bond strategy was used involving Acm protecting groups was used to fabricate the disulfide connectivity for α-conotoxins. To form the first disulfide bond the reduced peptides were dissolved in 0.1 M $NH_4HCO_3$ buffer (pH 8.2) at a concentration of 0.2 mg/mL, stirred overnight at room temperature, then purified by RP-HPLC. In instances where the peptide comprises a second disulfide, the second disulfide bond was formed by treating the peptides with iodine under acidic conditions. The peptides were dissolved in buffer A (0.5 mg/mL), then $I_2$ in $CH_3CN$ was slowly added until the solution became yellow. The reaction mixture was stirred for 15 min at 37° C., then quenched by adding ascorbic acid until the mixture became colorless. The fully oxidized peptides were purified by RP-HPLC on a 0.5% buffer B/min gradient. Analytical RP-HPLC and ES-MS confirmed the peptide purity and molecular mass.

Example 2: Stability Trials in Electrophysiology Assay Buffer

Peptides were incubated at 0.5 mg/mL in 150 mM tetraethylammonium chloride (TEA-Cl), 2 mM $CaCl_2$), 10 mM D-glucose, 10 mM HEPES, pH 7.4 (adjusted with NaOH) for 24 hours at 22° C. At timepoints of 0, 1, 4 and 24 h 100 μL aliquots were removed and quenched with 100 μL of 4% TFA in water. The samples were then analyzed by RP-HPLC using a gradient of 5 to 50% B over 40 minutes on a $C_{18}$ column.

Example 3: General Procedures for Electrophysiology

*Xenopus* Oocytes

Two-electrode voltage clamp recordings from *Xenopus* oocytes were carried out at room temperature using a GeneClamp 500B amplifier (Molecular Devices Corp., Sunnyvale, Calif.) at a holding potential (HP) of −80 mV. Voltage-recording and current-injecting electrodes were pulled from borosilicate glass (GC150T-7.5, Harvard Apparatus Ltd., Holliston Mass.) and had resistances of 0.3-1 MΩ when filled with 3 M KCl. Oocytes were perfused with ND96 solution at a rate of ~2 ml/min using a continuous push/pull syringe pump perfusion system. Inward currents through α7 or α9α10 nAChRs were evoked by applying 100 or 50 μM acetylcholine (ACh), respectively. Washout periods of 3 min between applications of ACh were used. Oocytes were incubated with peptides for 5 minutes before ACh was co-applied. All solutions contained 0.1% bovine serum albumin (Sigma-Aldrich). Peak ACh-evoked current amplitude was recorded before and after peptide incubation using pClamp 9 software (Molecular Devices Corp.).

Dorsal Root Ganglion (DRG) Neuron Preparation and Culture

Wistar rats were killed by cervical dislocation, as approved by the Animal Ethics Committee of RMIT University. DRG neurons were enzymatically dissociated from ganglia of 3-14-day-old Wistar rats as previously described (Callaghan et al., 2008). Cells were plated on poly-D-lysine/laminin-coated 12 mm round coverslips (BD Biosciences, Bedford, Mass., USA), incubated at 37° C. in high relative humidity (95%) and controlled $CO_2$ level (5%), and used within 16-36 h.

In DRG neurons, membrane currents through high-voltage-activated calcium channels (HVACC) were recorded in the whole-cell configuration of the patch clamp technique with an Axopatch 700B amplifier (Molecular Devices Corp., Sunnyvale, Calif.) at room temperature (22-24° C.). DRG neurons were transferred into a small-volume (~200 μl) recording chamber, which was constantly perfused with an extracellular (bath) solution containing (in mM): 150 tetraethylammonium (TEA)-Cl, 2 $BaCl_2$, 10 D-glucose and 10 HEPES, pH 7.4. Various drugs and toxins were prepared from stock solutions diluted to the final concentration immediately before the experiment in the bath solution and were applied via perfusion. During recording, DRG neurons were constantly perfused with the extracellular solution using a gravity-fed perfusion system at a flow rate of ~600 μl/min. Fire-polished borosilicate (GC150TF-7.5, Harvard Apparatus Ltd.) patch pipettes with tip resistance values of 1.5-2.2 MΩ were filled with an intracellular solution containing (in mM): 140 CsCl, 1 $MgCl_2$, 4 MgATP, 0.1 Na-GTP, 5 1,2-bis(O-aminophenoxy)ethane-N,N,N',N'-tetraacetic acid tetracesium salt (BAPTA)-$Cs_4$, and 10 HEPES-CsOH, pH 7.3. $Ba^{2+}$ currents ($I_{Ba}$) were filtered at 3 kHz and sampled at 10 kHz. Leak and capacitative currents were subtracted using a −P/4 pulse protocol. Data were stored digitally on a computer for further analysis.

In DRG neurons, relative peak current amplitude values (I/Icontrol) were determined from current amplitudes recorded in the absence (Icontrol) and presence of [$Ser^3$]Vc1.1(1-8), its analogues, or baclofen (bac) (I). Data are mean±SEM (n, number of experiments). Statistical analyses were performed in Sigma Plot 11.0 (Systat Software, Inc.) using Student's t test for two groups or one-way ANOVA with Bonferroni post-hoc testing for multiple comparisons. Differences were considered statistically significant at $P<0.05$.

Example 4: General Procedure for In Vitro Mouse Colonic Primary Afferent Recording Preparation In vitro single-unit extracellular recordings of action potential discharge were made from splanchnic colonic afferents. These recordings were made from C57BL/6 healthy or CVH mice using standard protocols. Baseline mechanosensitivity was determined in response to application of a 2 g vfh probe to the afferent receptive field for 3 s. This process was repeated 3-4 times, at 0.1 Hz. Mechanosensitivity was then re-tested after the application of increasing concentrations (1, 10, 100 and 1000 nM) of either [$Ser^3$]Vc1.1(1-8) or [$Ser^4$]Pu1.2(1-9). The peptides were applied to the mucosal surface of the colon for a period of 10 minutes at each concentration via a small metal ring placed over the receptive field of interest.

Example 5: General Procedure for NMR Analysis of Peptides

Peptides were dissolved in 90% $H_2O$/10% $D_2O$ or 99.96% $D_2O$ (Cambridge Isotope Laboratories) at a concentration of 1 mM and pH ~3.6. Spectra were recorded on a Bruker Avance-600 at 280 K and referenced to 4,4-dimethyl-4-silapentane-1-sulfonic acid at 0 ppm. Standard Bruker pulse programs were used for all two-dimensional spectra. Excitation sculpting with gradients was used to achieve water suppression for TOCSY and NOESY experiments.[4]

NMR experiments included TOCSY[5] using a MLEV-17 spin lock sequence with a 80 ms mixing time, NOESY[6] with a 200 ms mixing time, DQF-COSY[7], E.COSY[8], $^1H$-$^{13}C$ HSQC[9] and $^1H$-$^{15}N$ HSQC.[9] Spectra were recorded with 4096 data points in the F2 dimension and 512 increments in the F1 dimension for TOCSY, NOESY, DQF-COSY and E.COSY experiments and 2048×240 for $^1H$-$^{13}C$ HSQC and 2048×128 for $^1H$-$^{15}N$ HSQC data points in the F2 dimension and increments in the F1 dimension, respectively. The t1 dimension was zero-filled to 1024 real data points, and the F1 and F2 dimensions were multiplied by a sine-squared function before Fourier transformation.

Example 6: Controls and Standards

Where appropriate, the activity and/or physicochemical properties of the peptides were compared with the corresponding native full length peptides, Pu1.2, Vc1.1, Pn1.2 and RgIA. These native peptides were prepared in accordance with the general procedures described above, having the following formula:

```
                                        SEQ ID No. 40
G C C S D P R C N Y D H P E I C
(native full length Vc1.1)

                                        SEQ ID No. 41
G G C C S Y P P C I A N N P L C
(native full length Pu1.2)

                                        SEQ ID No. 42
G C C S H P P C F L N N P D Y C
(native full length Pn1.2)

                                        SEQ ID No. 43
G C C S D P R C R Y R C R C
(native full length RgIA)
```

The specific GABABR agonist baclofen was also used as a positive control where appropriate.

Globular, ribbon and beads isomers of full length peptides Pn1.2, Pu1.2 and Vc1.1 were prepared (using a regioselective disulfide strategy) and all were found to inhibit HVA calcium currents in rat DRG neurons (See FIG. 1, bead (blue), globular (green) and ribbon (red) isomers of α-conotoxins). Baclofen (bac) was used as a positive control (FIG. 1: bac, 50 μM, orange).

Example 7: Preparation of Peptides

Figure 9:
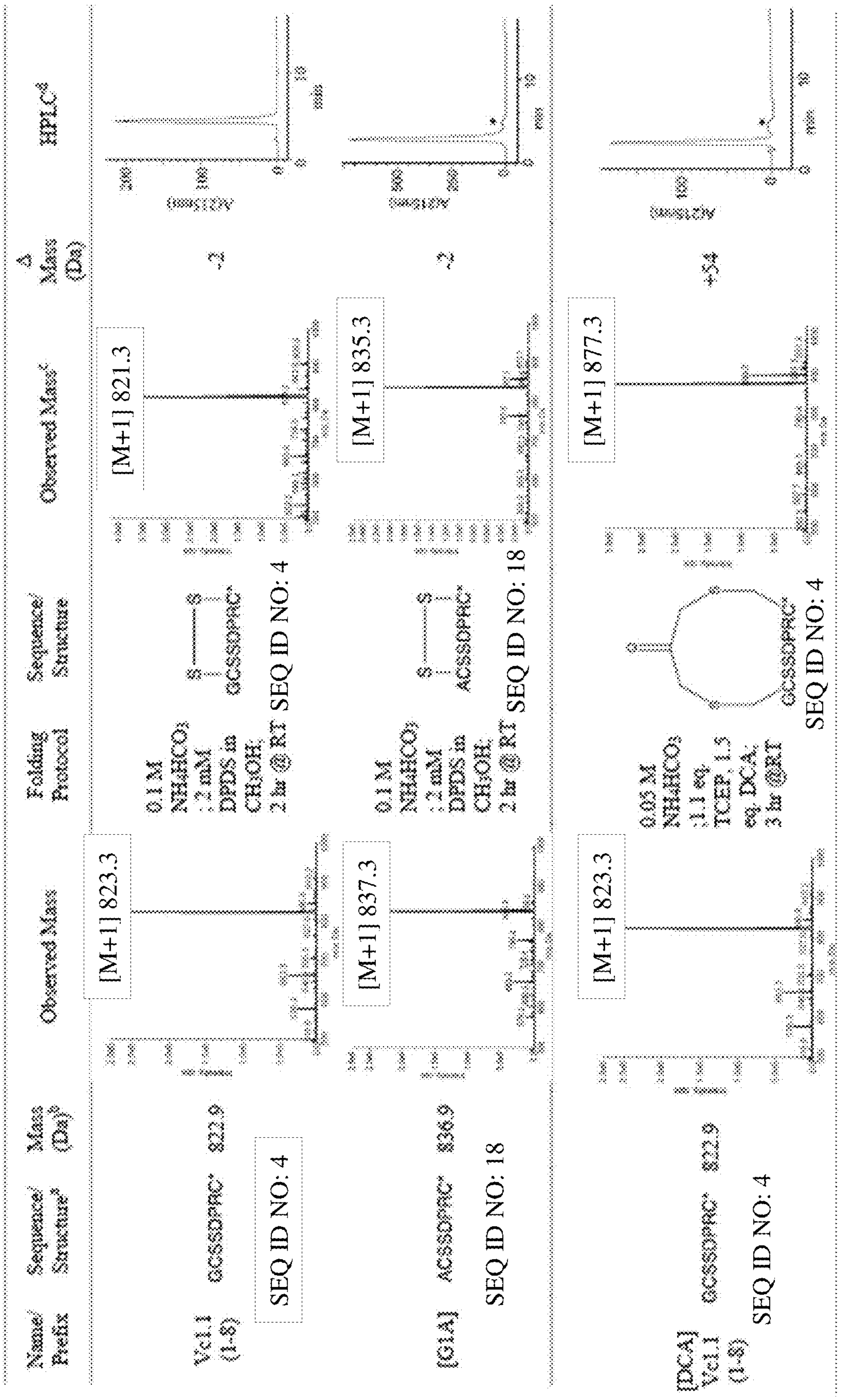
FIG. 9: Formula of representative peptides.
Figure 9:
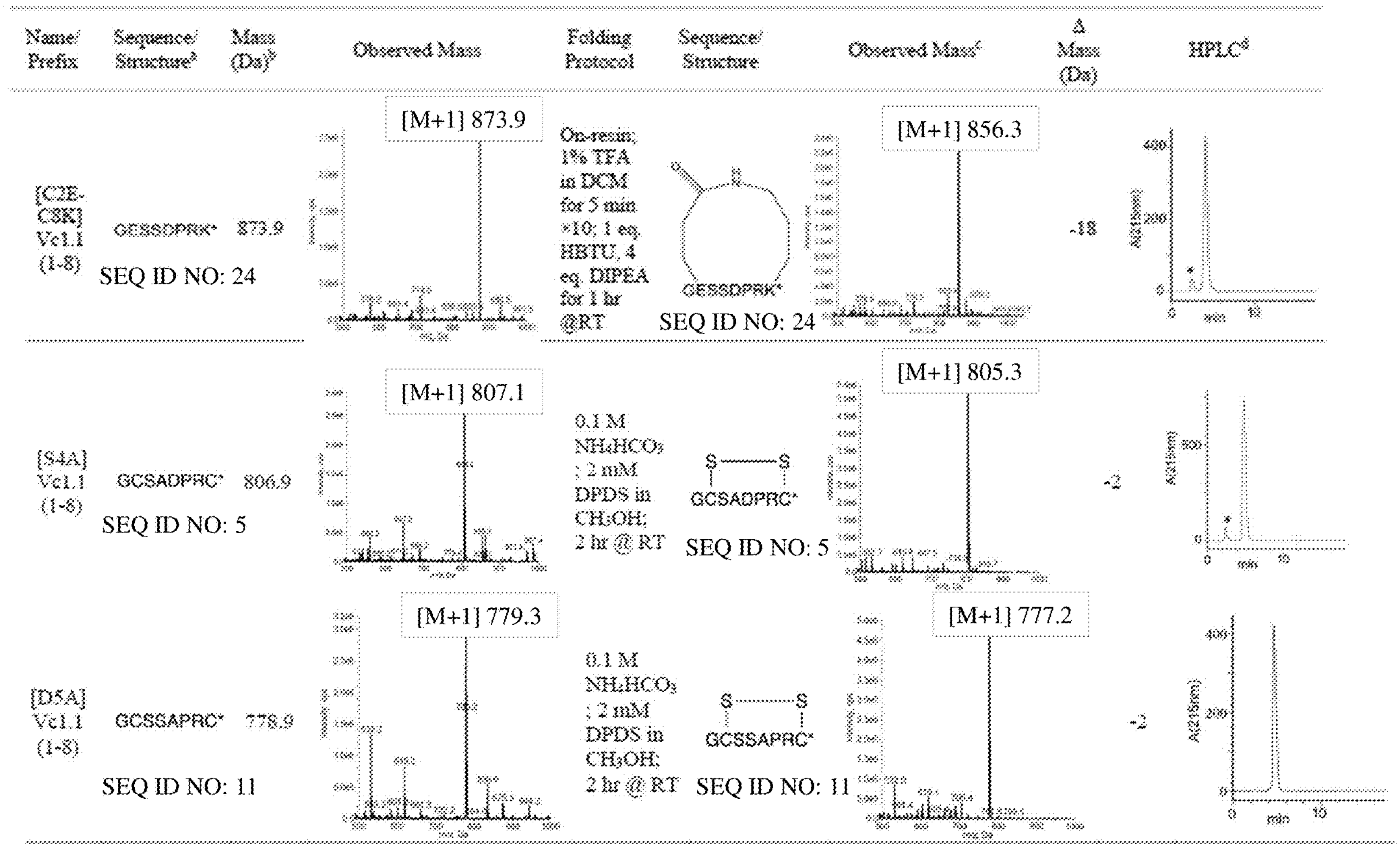
Figure 9:
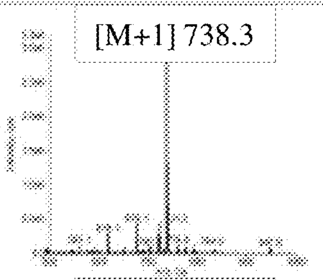
Figure 9:
Figure 9:
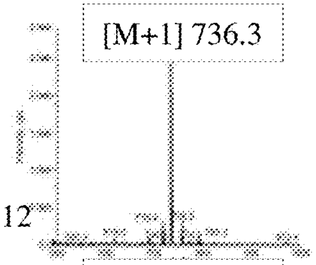
Figure 9:
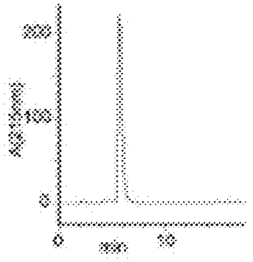
Figure 9:
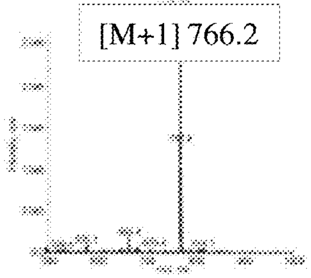
Figure 9:
Figure 9:
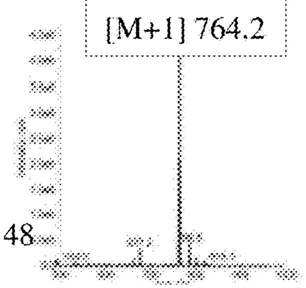
Figure 9:
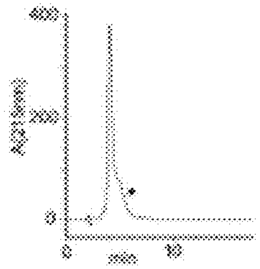
Figure 9:
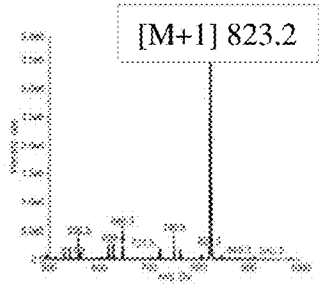
Figure 9:
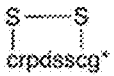
Figure 9:
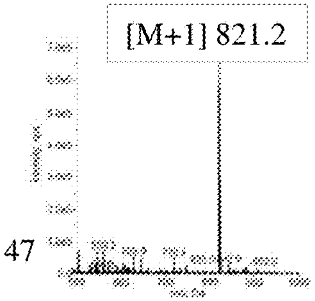
Figure 9:
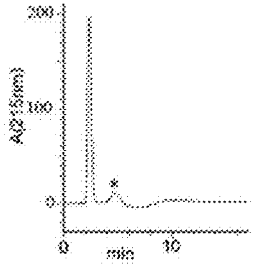

Representative peptides were prepared in accordance with the general procedures described above, having the following formula shown in FIG. 9.

Figure 2:
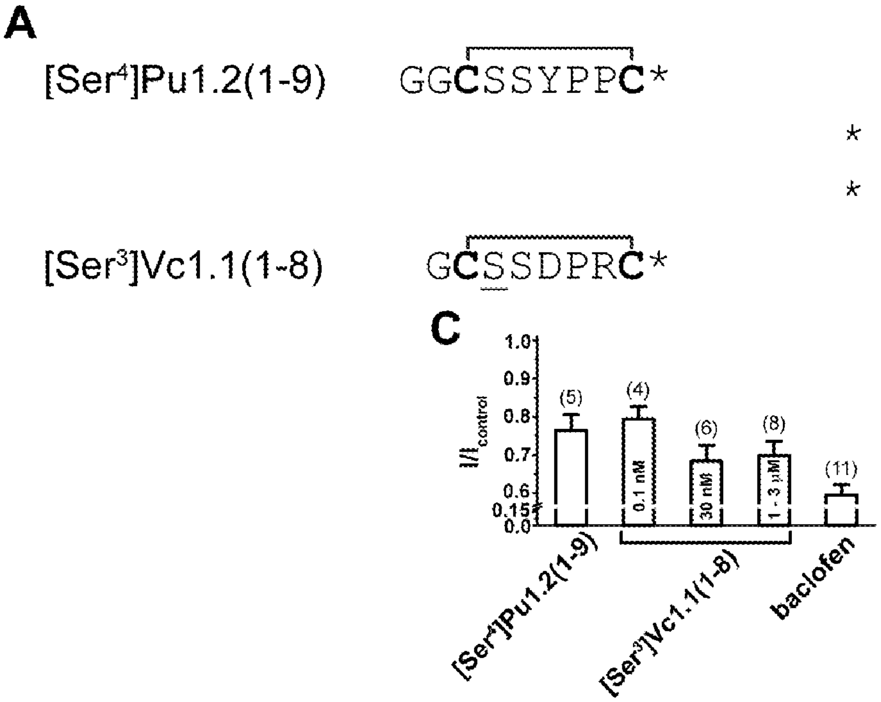
FIG. 2: Activity and/or physicochemical properties of truncated analogues of Pu1.2 and Vc1.1 in HVA calcium currents in rat and mouse DRG neurons. (A) The sequences of the truncated analogues of [Ser$^4$]Pu1.2(1-9) and [Ser$^3$]Vc1.1(1-8). Disulfide bonds are indicated by a solid line. The asterisk indicates an amidated C-terminus and the positions of the cysteines that have been substituted with serine are underlined. (C) Average $I/I_{control}$ data (±SEM) of peak $I_{Ca}$ inhibition in mouse DRG neurons. $I_{Ca}$ was inhibited by 23.5±4% (1 μM [Ser$^4$]Pu1.2(1-9)), 30.2±3.9%, 31.6±4% and 20.6±3.3% (1-3 μM, 30 nM and 100 pM [Ser$^3$]Vc1.1(1-8), respectively, or 41.5±2.7% (50 μM baclofen). The number of experiments is in parentheses.

Example 8: Comparison of Full Length and Truncated α-Conotoxins in HVA Calcium Currents in Rat and Mouse DRG Neurons The activity of two representative peptides, [Ser$^4$]Pu1.2 (1-9) and [Ser$^3$]Vc1.1(1-8), was examined in HVA calcium currents in rat and/or mouse DRG neurons. Both [Ser$^4$]Pu1.2 (1-9) and [Ser$^3$]Vc1.1(1-8) inhibited HVA calcium currents in rat or mouse DRG neurons (Refer to FIG. 2). As summarised in FIG. 2, average $I/I_{control}$ data (±SEM) of peak $I_{Ca}$ inhibition in mouse DRG neurons, $I_{Ca}$ was inhibited by 23.5±4% 1 μM [Ser$^4$]Pu 1.2(1-9), 30.2±3.9%, 31.6±4% and 20.6±3.3% 1-3 μM, 30 nM and 100 pM [Ser$^3$]Vc1.1(1-8), respectively, or 41.5±2.7% 50 μM baclofen. Baclofen (bac) was used as a positive control. Results were comparable to corresponding full length peptides.

Specifically, [Ser$^4$]Pu1.2(1-9) transiently inhibited peak $I_{Ca}$ by ~20%. The effect of [Ser$^4$]Pu1.2(1-9) could be reversibly antagonized by CGP55845 (1 μM). In mouse DRG neurons, [Ser$^3$]Vc1.1(1-8) (100 pM) inhibited $I_{Ca}$ by ~20% 1 μM [Ser$^3$]Vc1.1(1-8) resulted in ~30% inhibition in a faster (~3-5 min) time (FIG. 2). [Ser$^3$]Vc1.1(1-8) (1 μM) also inhibited HVA calcium currents by 25.1±6% in rat DRG neurons.

TABLE 4

Comparison of full-length and truncated α-conotoxin and baclofen activities at HVA calcium channels in rodent DRG neurons.

| Compound (concentration) | rat HVA $Ca^{2+}$ channel $I/I_{control}$ ± SEM (n) | mouse HVA $Ca^{2+}$ channel $I/I_{control}$ ± SEM (n) |
|---|---|---|
| Pn1.2 (1 μM) | 0.78 ± 0.03 (11) | ND |
| Pu1.2 (1 μM) | 0.73 ± 0.02 (12) | ND |
| Pu1.2(9-16) (1 μM) | 1.00 ± 0.00 (5) | ND |
| [Ser$^4$]Pu1.2(1-9) (1 μM) | 0.81 ± 0.03 (7) | 0.76 ± 0.04 (5) |
| Vc1.1 (1 μM) | 0.73 ± 0.03 (4) | ND |
| [Ser$^3$]Vc1.1(1-8) (1 μM) | 0.75 ± 0.06 (3) | 0.69 ± 0.04 (6) |
| Baclofen (50 μM) | 0.64 ± 0.01 (33) | 0.60 ± 0.03 (11) |

Values represent average relative peak current amplitudes ($I/I_{control}$) ± SEM; n, number of experiments; ND, not determined.

Figure 4:
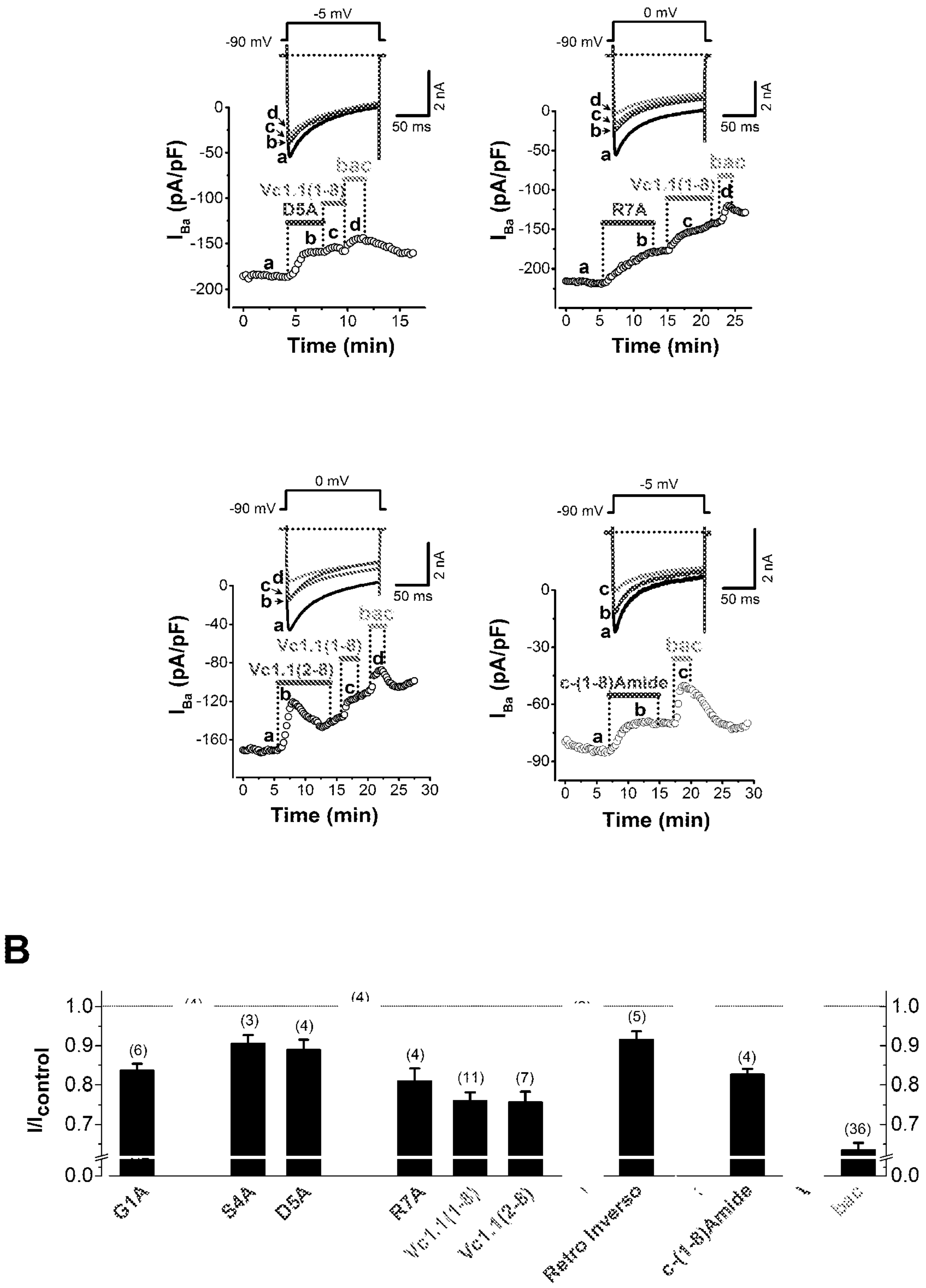
FIG. 4: Differential potencies of [Ser$^3$]Vc1.1(1-8) analogues at HVACCs in rat DRG neurons. Note that $I_{Ba}$ inhibition by baclofen (bac) is reversible on washout, whereas most [Ser$^3$]Vc1.1(1-8) analogues irreversibly inhibit $I_{Ba}$. A, Time course of peak $I_{Ba}$ in the presence of 1 μM of [D5A]Vc1.1(1-8) (D5A), [R7A]Vc1.1(1-8) (R7A), [Ser$^3$]Vc1.1(2-8) (Vc1.1(2-8)), Vc1.1(1-8)-Amide (c-(1-8) Amide)), and the specific $GABA_B$ receptor agonist baclofen (bac; 50 μM). Bars indicate the duration of peptide or baclofen application. Inward $I_{Ba}$ were evoked by voltage steps at 0.066 Hz, from a holding potential of −90 mV to 0 or −9 mV, respectively (top insets). Superimposed representative $I_{Ba}$ traces (insets), obtained in the absence (control), and presence of peptide or 50 μM baclofen, are shown at the times indicated by lowercase letters; dotted lines indicate zero current level. B, Bar graph summary of average relative peak $I_{Ca}$ amplitudes ($I/I_{control}$±SEM) by 1 μM [Ser$^3$]Vc1.1(1-8) or [Ser$^3$]Vc1.1(1-8) analogue, or 50 μM baclofen. The number of experiments, n, is in parentheses.

Example 9: Modulation of $Ba^{2+}$ Currents by [Ser$^3$]Vc1.1(1-8) Analogues in Rat DRG Neurons The modulation of $Ba^{2+}$ current ($I_{Ba}$) through HVACCs by nine α-conotoxin [Ser$^3$]Vc1.1(1-8) analogues in freshly isolated DRG neurons was examined. At 1 μM concentration. Retro-Inverso-Vc1.1(1-8), [S4A]Vc1.1(1-8), and [D5A]Vc1.1(1-8) irreversibly inhibited ~10% of peak $I_{Ba}$ amplitude (FIG. 4 and Table 4). Two of the Vc1.1(1-8) analogues, [R7A]Vc1.1(1-8) (1 μM) and Vc1.1(1-8)-Amide (1 μM), resulted in ~20% of peak $I_{Ba}$ amplitude inhibition. Similar to [Ser$^3$]Vc1.1(1-8) (control), [Ser$^3$]Vc1.1(2-8) (1 μM) also inhibited peak $I_{Ba}$ by ~25% (Table 5), however the effect was transient and ~60% of the inhibited $I_{Ba}$ fraction recovered in a relatively fast time-course process (FIG. 4). In these experiments, the $GABA_B$ receptor agonist baclofen (50 μM) was used as positive control. In cells showing diminished or absence of $I_{Ba}$ inhibition after Vc1.1(1-8) analogue exposure, subsequent application of baclofen suppressed a relatively large fraction (~35%) of total $I_{Ba}$. However, this baclofen-sensitive $I_{Ba}$ fraction was reduced (~10%) after [R7A]Vc1.1(1-8), Vc1.1(1-8), Vc1.1(1-8)-Amide, [Ser$^3$]Vc1.1(2-8), or [Ser$^3$]Vc1.1(1-8) exposure, consistent with an overlap between the intracellular signaling mechanisms induced by these two compounds (Callaghan et al., 2008; Berecki et al., 2014) (FIG. 4).

TABLE 5

Comparison of [Ser$^3$]Vc1.1(1-8) analogues and baclofen activities at $I_{Ba}$ through HVACCs in rat DRG neurons.

| Compound (concentration) | $I_{Ba}$ $I/I_{control}$ ± SEM (n) |
|---|---|
| [G1A]Vc1.1(1-8 (1 μM) | 0.84 ± 0.017 (6) |
| [S4A]Vc1.1(1-8) (1 μM) | 0.91 ± 0.021 (3) |
| [D5A]Vc1.1(1-8) (1 μM) | 0.89 ± 0.025 (4) |
| [R7A]Vc1.1(1-8) (1 μM) | 0.81 ± 0.032 (4) |
| [Ser$^3$]Vc1.1(1-8) (1 μM) | 0.76 ± 0.022 (11) |
| [Ser$^3$]Vc1.1(2-8) (1 μM) | 0.76 ± 0.026 (7) |

TABLE 5-continued

Comparison of [Ser3]Vc1.1(1-8) analogues and baclofen activities at $I_{Ba}$ through HVACCs in rat DRG neurons.

| Compound (concentration) | $I_{Ba}$ $I/I_{control}$ ± SEM (n) |
|---|---|
| Retro-Inverso-Vc1.1(1-8) (1 μM) | 0.91 ± 0.021 (5) |
| cVc1.1(1-8)-Amide (1 μM) | 0.83 ± 0.014 (4) |
| Baclofen (50 μM) | 0.64 ± 0.018 (36) |

Values represent average relative peak current amplitudes ($I/I_{control}$) ± SEM; n, number of experiments. Note that in our previous study, similar $I/I_{control}$ were found for [Ser3]Vc1.1 (1-8) (1 μM) in mouse and rat DRG neurons (Carstens et al, 2015).

Example 10: Comparison of Full Length and Truncated α-Conotoxins Activity of Pn1.2, Pu1.2, [Ser4]Pu1.2(1-9) and [Ser3]Vc1.1(1-8) at Human α7 and α9α10 nAChRs As described above, α-conotoxins target neuronal-type nAChRs with varying degrees of affinity and potency. It had been demonstrated that full length native α-conotoxin Vc1.1 inhibits rat and human α9α10 nAChRs in a concentration-dependent manner, with half-maximal inhibitory concentration ($IC_{50}$) values of 64 nM[46] and 765 nM[47], respectively, and weak inhibitory effect at α7 nAChRs ($IC_{50}$≅7.1 μM). The effect of α-conotoxins Pn1.2 (3 μM), Pu1.2 (3 μM), [Ser4]Pu1.2(1-9) (3 μM), and [Ser3]Vc1.1(1-8) (1 μM) was examined on the ACh-induced currents in *Xenopus* oocytes expressing human α7 or α9α10 nAChRs (and Table 6). [Ser3]Vc1.1(1-8) did not affect α9α10 nAChRs but stopped current through α7 nAChRs.

TABLE 6

Comparison of Pn1.2, Pu1.2, and the truncated α-conotoxins [Ser4]Pu1.2(1-9) and [Ser3]Vc1.1(1-8) activity at human α7 and α9α10 nAChRs in *Xenopus* oocytes.

| Compound | human α7 nAChR $I/I_{control}$ ± SEM (n) | human α9α10 nAChR $I/I_{control}$ ± SEM (n) |
|---|---|---|
| Pn1.2 (3 μM) | 0.006 ± 0.005 (5) | 0.012 ± 0.001 (4) |
| Pu1.2 (3 μM) | 0.98 ± 0.03 (6) | 1.01 ± 0.04 (4) |
| [Ser4]Pu1.2(1-9) (3 μM) | 0.99 ± 0.03 (5) | 1.04 ± 0.03 (3) |
| [Ser3]Vc1.1(1-8) (1 μM) | 0.057 ± 0.008 (6) | 1.07 ± 0.04 (3) |

Values represent average relative peak current amplitudes ($I/I_{control}$) ± SEM; n, number of experiments. Data were acquired with 100 μM ACh for α7 nAChRs or 50 μM ACh for α9α10 nAChRs.

Example 11: Activity of [Ser3]Vc1.1(1-8) Analogues at Human α7 (A) and Human α9α10 nAChRs (B) Expressed in *Xenopus* Oocytes Experiments were conducted in accordance with the general procedures outlined above. Results are summarised in Table 7.

TABLE 7

Comparison of activities of Vc1.1, cVc1.1, [E14DapAc]cVc1.1, truncated α-conotoxin [Ser3]Vc1.1(1-8) and [Ser3]Vc1.1(1-8) analogues at human α7 and α9α10 nAChRs in *Xenopus* oocytes.

| Compound | human α7 nAChR $I/I_{control}$ ± SEM (n) | human α9α10 nAChR $I/I_{control}$ ± SEM (n) |
|---|---|---|
| Vc1.1 (1 μM) | N.D. | 0.57 ± 0.020 (17) |
| [Ser3]Vc1.1(1-8) (3 μM) | 0.05 ± 0.017 (10) | 1.04 ± 0.041 (14) |
| [G1A]Vc1.1(1-8) (3 μM) | 0.36 ± 0.038 (8) | 1.05 ± 0.027 (13) |
| [S4A]Vc1.1(1-8) (3 μM) | 0.08 ± 0.007 (5) | 1.03 ± 0.046 (12) |
| [R7A]Vc1.1(1-8) (3 μM) | 1.03 ± 0.027 (11) | 1.06 ± 0.024 (16) |
| [Ser3]Vc1.1(2-8) (3 μM) | 1.01 ± 0.019 (8) | 1.03 ± 0.009 (7) |
| Vc1.1(1-8)-Amide (3 μM) | 1.05 ± 0.017 (8) | 1.04 ± 0.022 (9) |
| [E14DapAc]cVc1.1 (3 μM) | 1.08 ± 0.019 (8) | 0.52 ± 0.026 (6) |

Values represent average relative peak current amplitudes ($I/I_{control}$) ± SEM; n, number of experiments. Data were acquired with 100 μM ACh for α7 nAChRs or 6.5 μM ACh for α9α10 nAChRs.
N.D., not determined.

Example 12: Colonic Nociceptor Function

Figure 3:
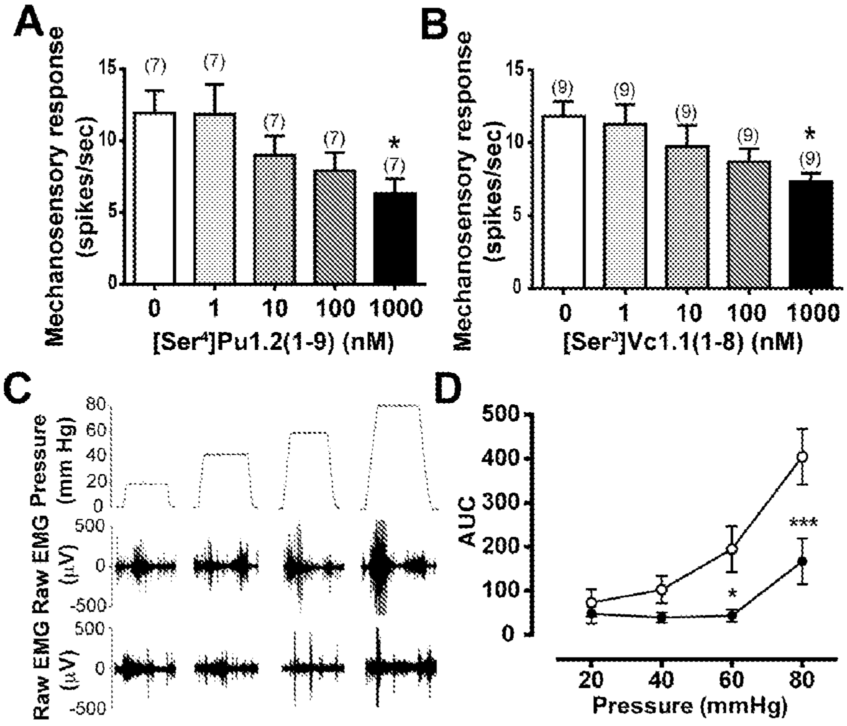
FIG. 3: (A) [Ser$^4$]Pu1.2(1-9) significantly inhibits splanchnic colonic nociceptors from healthy mice. Compared with baseline, [Ser$^4$]Pu1.2(1-9) at 1000 nM significantly reduced colonic nociceptor mechanosensitivity (*P<0.05, n=7 afferents, one-way ANOVA, Bonferroni-posthoc). (B) [Ser$^3$]Vc1.1(1-8) also reduced colonic nociceptor mechanosensitivity, with significant reductions in mechanical responses observed at a concentration of 1000 nM (*P<0.05, n=9 afferents, one-way ANOVA, Bonferroni-posthoc). (C) Representative tracing of the VMR to colorectal distension in mice. The upper panel shows the distension sequence (20 s duration, 4 min interval). The corresponding EMG recordings after vehicle and 1000 nM [Ser$^3$]Vc1.1(1-8) are illustrated in the middle and lower panel respectively. VMR to colorectal distension were notably reduced by [Ser$^3$]Vc1.1(1-8). (D) Intracolonic treatment with [Ser$^3$]Vc1.1(1-8) significantly reduced VMR to 60 and 80 mmHg of distension in healthy control (HC) mice. Data expressed as area under the curve of the corresponding EMG signal for n=4/group. Two-way ANOVA followed by Bonferroni post hoc test; * p<0.05, *** p<0.001.

Representative peptides, [Ser4]Pu1.2(1-9) or [Ser3]Vc1.1 (1-8) were examined for their ability to modify colonic nociceptor function, in accordance with the general procedure outlined above, using ex vivo afferent recordings from mouse splanchnic high-threshold nociceptors which respond to focal compression and noxious stretch/distension. Nociceptor mechanosensitivity was assessed before and after increasing doses of each peptide. Results are summarized in FIG. 3. [Ser4]Pu1.2(1-9) dose-dependently inhibited colonic nociceptor mechanosensitivity, with greatest inhibition observed at a concentration of 1000 nM [Ser4]Pu1.2(1-9) (FIG. 3A). [Ser3]Vc1.1(1-8) also inhibited nociceptor mechanosensitivity at a concentration of 1000 nM (FIG. 3B). Overall, [Ser4]Vc1.2(1-9) and [Ser3]Vc1.1(1-8) both induced similar levels of nociceptor inhibition at 1000 nM. The effect of [Ser3]Vc1.1(1-8) was also examined in a mouse model of visceral pain. Noxious distension of the colorectum triggers the visceromotor response (VMR), a nociceptive brainstem reflex consisting of the contraction of the abdominal muscles. Using abdominal electromyography (EMG), this technique allows assessing visceral sensitivity in vivo in fully awake animals. In this model, intracolonic treatment with [Ser3]Vc1.1(1-8) significantly reduced VMR in response to colorectal distension compared to vehicle treated mice (FIGS. 3C and D).

Example 13: Treatment of Neuropathic Pain

A representative peptide [Ser3]Vc1.1(1-8) was assessed in a rat model for neuropathic pain. Single subcutaneous (s.c.) bolus doses of [Ser3]Vc1.1(1-8) was examined relative to a positive control (gabapentin) and vehicle (sterile water for injection; WFI) in male Sprague-Dawley rats with a unilateral chronic constriction injury (CCI) of the sciatic nerve, a widely utilized rat model of neuropathic pain.

Experiments were performed on 32 male Sprague-Dawley rats weighing 200-225 g at 6-8 weeks old. Rats underwent partial ligation of the left sciatic nerve (PNL) (Seltzer et al., 1990), as previously described (Ekberg et al., 2006). Rats received a single bolus dose of the test item or controls according to a 'washout' protocol with a minimum 48 hour washout period between successive doses.

TABLE 8

Summary of doses (n ≥ 6 per dose level)

| | |
|---|---|
| N ≥ 6 Gabapentin (positive control) | 100 mg/kg |
| N ≥ 6 Vehicle (WFI) (control) | 2 mL/kg |

TABLE 8-continued

| Summary of doses (n ≥ 6 per dose level) | |
|---|---|
| N ≥ 6 Vc1.1 (1-8) | 1 mg/kg |
| N ≥ 6 Vc1.1 (1-8) | 3 mg/kg |
| N ≥ 6 Vc1.1 (1-8) | 10 mg/kg |

The study was conducted according to the following protocol: animals were acclimatised for at least 3 days prior to initiation of experimentation.

Day 0
- Baseline von Frey paw withdrawal thresholds (PWTs) determined
- Chronic constriction injury surgery
- Surgical recovery Day 1-13
- Once weekly baseline PWTs determined Day 14-28 (48 hr washout protocol; n≥6 per dose per compound or vehicle)
- Administer single bolus doses of test or control items via subcutaneous route
- Measure PWTs pre-dose and at the following post-dosing times, 15, 30, 45, 60, 75, 90, 120 and 180 min.

Figure 5:
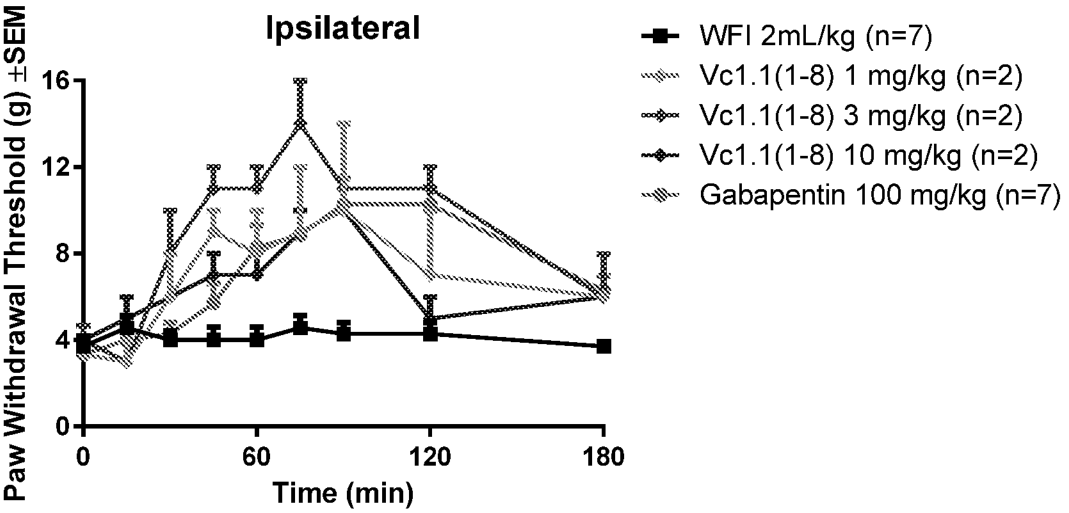
FIGS. 5 and 6: Administration of representative peptide [Ser$^3$]Vc1.1(1-8) in a rat model for neuropathic pain. Single subcutaneous (s.c.) bolus doses of [Ser$^3$]Vc1.1(1-8) was examined relative to a positive control (gabapentin) and vehicle (sterile water for injection; WFI) in male Sprague-Dawley rats with a unilateral chronic constriction injury (CCI) of the sciatic nerve, a widely utilized rat model of neuropathic pain.

The paw withdrawal threshold for the ipsilateral hindpaws of CCI-rats that responded following administration of single subcutaneous bolus doses of Water for Injection (WFI; n=7) at 2 mL/kg, Vc1.1(1-8) at 1, 3 or 10 mg/kg (n=2) or gabapentin at 100 mg/kg (n=7) at time 0 (pre-dosing) and at 15, 30, 45, 60, 75, 90, 120 and 180 min post-dosing is summarised in FIG. 5. Responders were defined as CCI-rats that evoked ≥4 g in any testing-time points compared to its averaged baseline PWTs after administration of Vc1.1(1-8) or gabapentin.

Rats treated with Vc1.1 (1-8) exhibited a reduction in neuropathic pain across all doses tested when compared with the water vehicle (WFI) (FIG. 5).

Figure 6:
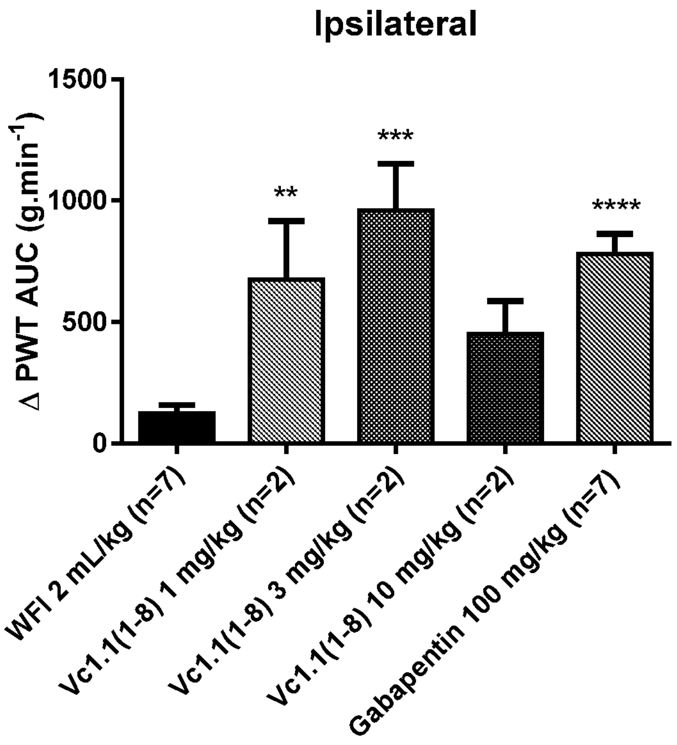

The mean (±SEM) extent and duration of action quantified as the mean (±SEM) areas under the Δ PWT versus time curves (Δ PWT AUC values) for the ipsilateral (injured side) hindpaws of CCI-rats that responded following administration of single subcutaneous bolus doses of WFI at 2 mL/kg (n=7), Vc1.1(1-8) at 1, 3 or 10 mg/kg (n=2) or gabapentin at 100 mg/kg (n=7) is summarised in FIG. 6. Responders were defined as CCI-rats that evoked ≥4 g in any testing-time points compared to its averaged baseline PWTs after administration of Vc1.1(1-8) or gabapentin.

p≤0.01 * p≤0.001 **** p≤0.0001

Note: Due to the low n-number (n=2), statistical analysis performed on the Vc1.1(1-8) are for indication only.

Example 14: Comparative Activity at α7 and α9α10 nAChR Acetylcholine

Figure 7:
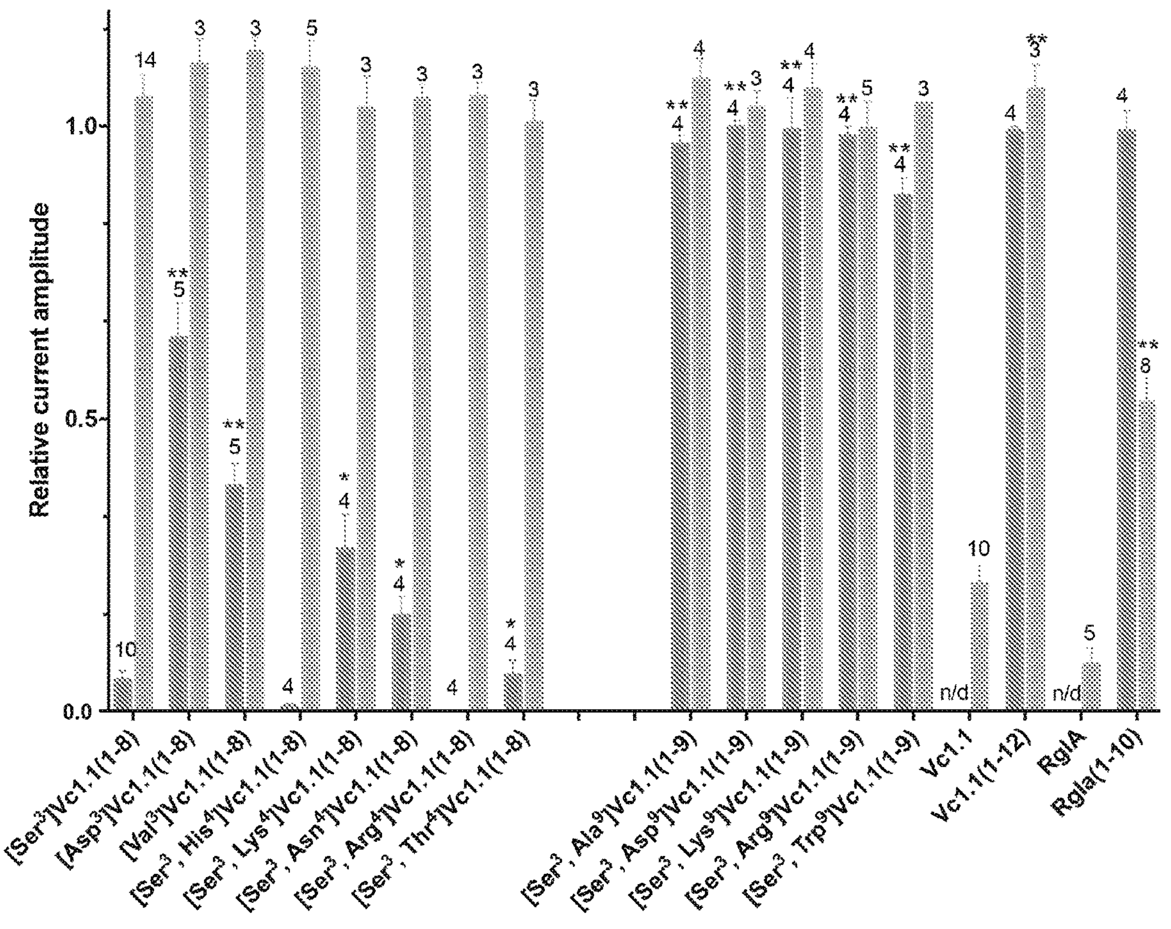
FIG. 7: Relative acetylcholine induced current amplitude at α7 (blue) and α9α10 (orange) nAChR after incubation with various [Ser$^3$]Vc1.1(1-8) analogues at 3 μM.

Acetylcholine (ACh) induced current amplitude was assessed at α7 and α9α10 nAChR after incubation with various [$Ser^3$]Vc1.1(1-8) analogues at 3 μM. Results are summarised in FIG. 7.

Human α7 and α9α10 nAChR were expressed in stage V-VI *Xenopus laevis* oocytes and two-electrode voltage clamp recordings were conducted at 21-24° C. at pH 7.4. Acetylcholine (ACh) applications were the corresponding $EC_{50}$s; 200 μM for α7 and 6 μM for α9α10 nAChR. Oocytes were washed for 3 min between 3 ACh applications before 5 min incubation with peptide ACh was subsequently co-applied with the peptide and the resulting amplitude was divided by the initial acetylcholine only amplitude. Sample numbers are above corresponding bars with standard error of the mean. Data was analysed with an unpaired student t-test in Graphpad Prism where truncated Vc1.1 analogues (S3X, S4X, N9X) were compared against [$Ser^3$]Vc1.1(1-8), [Ser3]Vc1.1(1-12) and [Ser3]Vc1.1(1-8) were compared against Vc1.1, and RgIA (1-10) against RgIA at the α9α10 nAChR. *=p value<0.05, **=p value<0.0001, else not significant.

Example 15: Stability Profile of [$Ser^3$]Vc1.1(1-8) In Vitro

The stability of [$Ser^3$]Vc1.1(1-8) in human serum (FIG. 8A), simulated gastric fluid (SGF) (FIG. 8B) and simulated intestinal fluid (SIF) (FIG. 8C) was assessed over multiple time points using LC/MS. Results are summarised in FIG. 8.

The human serum stability assay was conducted at 25% serum to reduce speed of peptide degradation to allow identification of products. Human male AB serum (H4522 Sigma-Aldrich) was centrifuged at 14000 g for 10 minutes to remove the lipid component. Three replicates of 25% serum in 1×PBS and two controls (one replicate of 1×PBS, one replicate of 25% serum) were prepared and incubated at 37° C. for 10 minutes. Thereafter [Ser3]Vc1.1(1-8) dissolved in ultrapure water was added to triplicate 25% serum and PBS control tubes to reach a final concentration of 20 μM. Ultrapure water of the same volume was added to the 25% serum control tube. These were incubated at 37° C. with 40 μL aliquots taken at 0, 1, 5, 10, 15, 30, 60, 180, 360 and 1440 minutes. Each aliquot was quenched with 6M urea and incubated for 10 minutes at 5° C. Thereafter 40 μL of 20% trichloroacetic acid (TCA) was added and incubated for another 10 minutes at 5° C. They were then centrifuged at 14000 g for 10 minutes and the supernatant removed for LC/MS. The area under each peak was extracted from Analyst® Software and taken as a percentage of the combined 0 time point. Data was graphed on Graphpad Prism with a non-linear regression displaying mean and standard error of the mean (SEM) error bars for each time point.

Simulated gastric fluid and simulated intestinal fluid were prepared as per the US Pharmacopeia. SGF was prepared with 20 mg NaCl and 16 mg of pepsin (Sigma Aldrich 3200-4500 units/mg protein) in 70 μL of HCl with 10 mL of ultrapure water to reach a pH of 1.2. Four replicates of SGF and one ultrapure water control were incubated at 37° C. for 10 minutes. [$Ser^3$]Vc1.1(1-8) was added to three replicates and the ultrapure water control to reach a final concentration of 100 μg/mL while ultrapure water of the same volume was added to the last SGF replicate. These were incubated at 37° C. and 50 μL aliquots were taken at 0, 5, 15, 30, 60, 180, 360, 1440 and 2880 minutes. Each aliquot was quenched with 50 μL, of 0.5M $NaHCO_3$ and was analysed with LC/MS as per the human serum stability assay.

SIF was prepared with 68 mg of $KH_4PO_4$ in 250 μL of water, 770 μL of 0.2N NaOH, 5 mL of ultrapure water and 100 μg of porcine pancreatin (Sigma Aldrich activity equivalent to 8× U.S.P specifications). Replicates and controls were prepared as per SGF with incubation at 37° C. for 10 minutes before addition of [$Ser^3$]Vc1.1(1-8). A 504. aliquot was taken at the same time points used in SGF, however they were quenched with 50 μL of 4% TFA before LC/MS as per the human serum stability assay.

Figure 8:
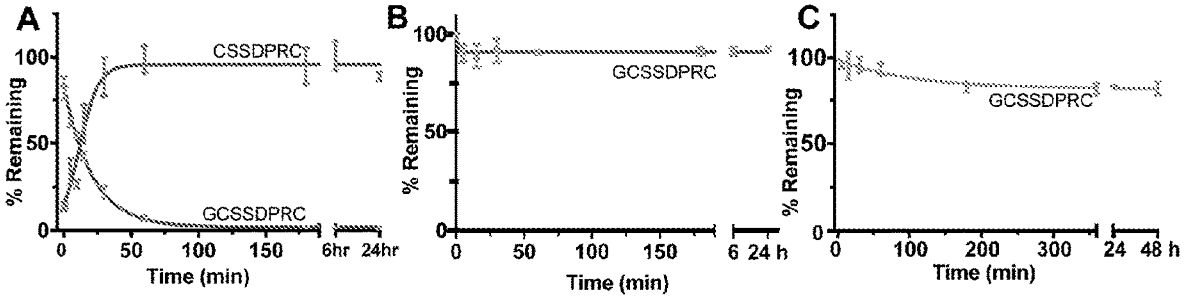
FIG. 8: Stability profile of [Ser$^3$]Vc1.1(1-8) in vitro; (A) Stability of [Ser$^3$]Vc1.1(1-8) (green) in human serum; (B) Stability of [Ser$^3$]Vc1.1(1-8) in simulated gastric fluid (made to U.S.P. specifications); and (C) Stability of [Ser$^3$]Vc1.1(1-8) in simulated intestinal fluid (made to U.S.P. specifications). Note: all experiments were performed in triplicate.

As summarised in FIG. 8; in the human serum stability assay the N-terminal residue of [$Ser^3$]Vc1.1(1-8) (green) was cleaved in <2 h to form [$Ser^3$]Vc1.1(2-8) (orange) (FIG. 8A). In simulated gastric fluid, [$Ser^3$]Vc1.1(1-8) exhibited good stability over a 24 h period (FIG. 8B). Additionally, in simulated intestinal fluid, only a small amount of [$Ser^3$]Vc1.1(1-8) was lost over the course of the assay. All experiments were performed in triplicate.

The claims defining the invention are as follows:

1. An isolated peptide comprising a truncated alpha-conotoxin peptide, wherein (a) said alpha-conotoxin peptide naturally comprises 4 cysteine residues, (b) said truncated alpha-conotoxin peptide comprises or consists of the sequence:

SEQ ID NO: 44

$Xaa_1$ $Xaa_2$ S $Xaa_4$ $Xaa_5$ P $Xaa_6$ $Xaa_7$ wherein (1) $Xaa_1$ is selected from glycine or alanine or is absent, (2) $Xaa_2$ and $Xaa_7$ correspond to cysteine residues 1 and 3 of the alpha-conotoxin peptide, and are (i) either cysteines linked together by a disulphide bond or acylthio linker or (ii) another pair of amino acids linked together through their side chains, and (3) $Xaa_4$, $Xaa_5$, and $Xaa_6$ are the corresponding amino acid residues of the alpha-conotoxin peptide, (c) said truncated alpha-conotoxin peptide does not comprise a cysteine corresponding to cysteine residue 4 of the alpha-conotoxin peptide, and (d) the serine in position 3 of SEQ ID NO: 44 corresponds to cysteine residue 2 of the alpha-conotoxin peptide.

2. The peptide according to claim 1, wherein Xaa2 and Xaa7 are each independently selected from cysteine, alanine, glutamic acid, aspartic acid, lysine, and ornithine.

3. The peptide according to claim 1, wherein $Xaa_2$ and $Xaa_7$ are each cysteine, the side chains of which together form a disulfide bond.

4. The peptide according to claim 1, wherein $Xaa_4$ is selected from serine, alanine, arginine, histidine, asparagine, lysine, aspartic acid and threonine.

5. The peptide according to claim 1, wherein Xaa5 is selected from alanine, aspartic acid, tyrosine, histidine and asparagine.

6. The peptide according to claim 1, wherein $Xaa_6$ is selected from arginine, proline, and alanine.

7. The peptide according to claim 1, wherein the peptide comprises or consists of the sequence:

SEQ ID NO: 4

G C S S D P R C.

8. The peptide according to claim 1, wherein the peptide further comprises one or more additional amino acids.

9. The peptide of claim 4, wherein the peptide comprises or consists of the sequence the sequence:

SEQ ID NO: 29
GGCSSYPPC.

10. The peptide according to claim 1 wherein the C-terminus of the peptide is a carboxyl group or a primary amide, or the C-terminus is linked to the N-terminus by a linker.

11. The peptide according to claim 1 wherein the C-terminus of the peptide is a primary amide.

12. The peptide according to claim 1 comprising or consisting of a sequence selected from the group consisting of:

| SEQ ID NO. | Sequence | Structure |
|---|---|---|
| SEQ ID No. 4 | G C S S D P R C* | 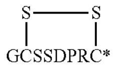 |
| SEQ ID No. 5 | G C S A D P R C* | 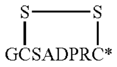 |
| SEQ ID No. 6 | G C S K D P R C* | 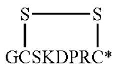 |
| SEQ ID No. 7 | G C S N D P R C* | 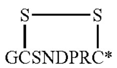 |
| SEQ ID No. 8 | G C S T D P R C* | 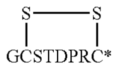 |
| SEQ ID No. 9 | G C S H D P R C* | 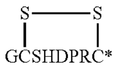 |
| SEQ ID No. 10 | G C S R D P R C* | 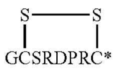 |
| SEQ ID No. 11 | G C S S A P R C* | 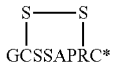 |
| SEQ ID No. 12 | G C S S D P A C* | 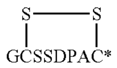 |
| SEQ ID No. 13 | G C S S N P A C* | 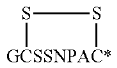 |
| SEQ ID No. 14 | G C S S D P R C* | 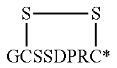 |
| SEQ ID No. 15 | G C S S H P A C* | 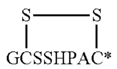 |
| SEQ ID No. 16 | G C S S Y P P C* | 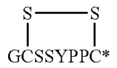 |
| SEQ ID No. 18 | A C S S D P R C* | 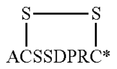 |
| SEQ ID No. 19 | C S S D P R C* | 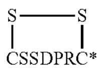 |

-continued

| SEQ ID NO. | Sequence | Structure |
|---|---|---|
| SEQ ID No. 29 | G G C S S Y P P C* | 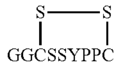 |
| SEQ ID No. 30 | G C S S D P R C A* | 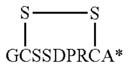 |
| SEQ ID No. 31 | G C S S D P R C W* | 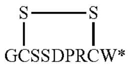 |
| SEQ ID No. 32 | G C S S D P R C R* | 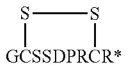 |
| SEQ ID No. 33 | G C S S D P R C K* | 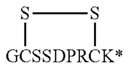 |
| SEQ ID No. 34 | G C S S D P R C D* | 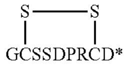 |
| SEQ ID No. 35 | G C S S D P R C R Y* | 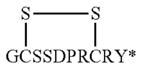 |
| SEQ ID No. 36 | G C S S D P R C N Y D H* | 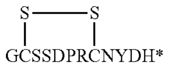 |
| SEQ ID No. 24 | G E S S D P R K* | 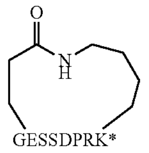 |
| SEQ ID No. 25 | G D S S D P R K* | 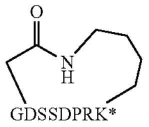 |
| SEQ ID No. 26 | G D S S D P R X*, wherein X denotes ornithine | 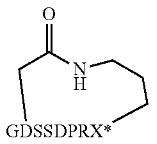 |
| SEQ ID No. 4 | G C S S D P R C* | 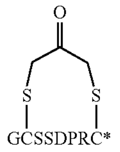 |
| SEQ ID No. 27 | G C S S D P R A* | 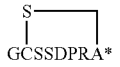 |
| SEQ ID No. 28 | G A S S D P R C* | 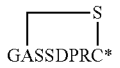 |
| SEQ ID No. 37 | C S S D P R C S S D P R* | 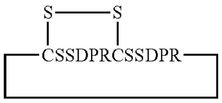 |

-continued

| SEQ ID NO. | Sequence | Structure |
|---|---|---|
| SEQ ID No. 38 | G C S S D P R C T K S I P P* | 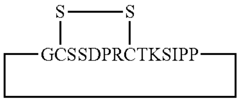 |
| SEQ ID No. 39 | G G C S S D P R C F P D* | 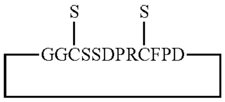 |

wherein * indicates that the C-terminus of the peptide is a primary amide.

13. A composition comprising the peptide according to claim 1 and a pharmaceutically acceptable carrier or diluent.

14. A method of treating pain, comprising administering to a person in need thereof, a therapeutically effective amount of the peptide according to claim 1.

15. A method of claim 14, wherein the pain is neuropathic pain.

16. A method of claim 14, wherein the pain is visceral pain.

* * * * *